US005543323A

United States Patent [19]

Ridley et al.

[11] Patent Number: 5,543,323

[45] Date of Patent: Aug. 6, 1996

[54] PLASMODIUM MEROZOITE RHOPTRIES ANTIGENIC POLYPEPTIDES

[75] Inventors: Robert G. Ridley; John G. Scaife, both of Edinburgh, Great Britain

[73] Assignee: Hoffman-La Roche Inc., Nutley, N.J.

[21] Appl. No.: 340,514

[22] Filed: Nov. 16, 1994

Related U.S. Application Data

[62] Division of Ser. No. 86,416, Jul. 1, 1993, abandoned, which is a continuation of Ser. No. 992,988, Dec. 18, 1992, abandoned, which is a continuation of Ser. No. 489,312, Mar. 5, 1990, abandoned.

[30] Foreign Application Priority Data

| | | | |
|---|---|---|---|
| Mar. 14, 1989 | [GB] | England | 8905857 |
| Aug. 22, 1989 | [GB] | England | 8919064 |

[51] Int. Cl.[6] .......... C12N 15/30; C12N 1/21; C12N 1/13; C12N 5/10

[52] U.S. Cl. .......... 435/252.3; 435/320.1; 435/252.33; 435/254.11; 435/69.3; 435/240.2; 536/23.1; 536/23.7; 935/65

[58] Field of Search .......... 536/23.1, 23.7; 435/320.1, 252.3, 252.33, 254.11, 69.1, 69.3, 240.2; 935/12, 65

[56] References Cited

U.S. PATENT DOCUMENTS

| | | | |
|---|---|---|---|
| 4,978,621 | 12/1990 | Ardeshir et al. | 435/252.3 |
| 5,116,755 | 5/1992 | Kemp et al. | 435/252.3 |

FOREIGN PATENT DOCUMENTS

| | | |
|---|---|---|
| WO84/02917 | 8/1984 | WIPO . |
| WO89/07645 | 8/1989 | WIPO . |

OTHER PUBLICATIONS

Schofield, L. et al. 1986. Molec. Biochem. Parasitol. vol. 18 pp. 183–195 (1986).

Kemp, D. J. et al. 1983. Proc. Natl. Acad. Sci. USA vol. 80 pp. 3787–3791.

Mierendorf, R. C. et al. 1987. Meth. Enzymol. vol. 152 pp. 458–469.

Harnyuttanakorn, P. et al. 1992. Molec. Biochem. Parasitol. vol 55 p. 177–186.

Braun–Berton, E. et al., Activation of a *Plasmodium falciparum* protease correlated with merozoite maturation and erythrocyte invasion, Biol. Cell, 64(2), 223–231 (1988).

Hall et al, Molec & Biochem. Parasit., 7:247–265 (1983).

Clark et al., Parasitol Res. 73: 425–434 (1987).

Bushell, et al., Molec & Biochem. Parasit. 28:105–112 (1988).

Crewther, et al., Experimental Parasit. 70: 193–206 (1990).

Crewther et al., Bio. Abst., 89: Abstract No. 94185 (1990).

Culvenor et al., J. Protozool., 37:59–65 (1990).

Favaloro et al., Mol. Biochem. Parasitol., 32: 297–299 (1989).

Peterson et al., Mol. Cell. Biol., 9:3151–3154 (1989).

Campbell et al., Am. J. Trop. Med. Hyg., 33:1051–1054 (1984).

Howard et al., Am. J. Trop. Med. Hyg., 33:1055–1059 (1984).

Scaife J., Genetic Engineering 7:57–90 (1988).

Braun–Breton et al., Nature, 332:457–459 (1988).

*Primary Examiner*—Mary E. Mosher

*Attorney, Agent, or Firm*—George M. Gould; William H. Epstein; Catherine A. Picut

[57] ABSTRACT

Novel antigenic polypeptides having at least one determinant immunologically cross-reactive with determinants on a polypeptide associated with the rhoptry organelles of the merozoite form of the malaria parasite Plasmodium falciparum are described. Also described are immunogenic compositions containing such a polypeptide, DNAs coding for such a polypeptide, recombinant vectors containing such a DNA sequence, host organisms containing a replicable vector, and antibodies which are directed against a polypeptide in accordance with the invention. In addition, processes for the production of the immunogenic compositions, the microorganisms, and the antibodies, as well as the use the polypeptides and the immunogenic compositions for the immunization of mammals against malaria are also described.

6 Claims, 3 Drawing Sheets

-116 AATTGTAATACTCACATATATATATATATATATATATAT
-79 ATATTTATTTATTTATTTATTTATTTATTTATTTATATAGTAAAAAATCAATTAATTTTTTTTTTTTTTTTATATATA

1 ATG AGT TTC TAT TTG GGT AGC TTA GTA ATA ATA TTC CAT GTA CTC TTC CGT AAT GTC GCT
1 M S F Y L G S L V I I F H V L F R N V A

61 GAT GGT ATA AAT GTA AAC GGA GAT AAT AAT TAT GGG AAA ACA ATA ATC AAT AAT GAT TTC
21 D G I N V N G D N N Y G K T I I N N D F

121 AAT TTT GAT GAT TAC AAT TAT TGG ACA CCA ATA AAT AAA AAG GAA TTT TTA AAT TCC TAT
41 N F D D Y N Y W T P I N K K E F L N S Y

181 GAA GAT GAA TTT TCA AGT GAA TCC TTT TTA GAA AAT AAA TCT AGT GTT GAT GAT GGA AAT
61 E D E F S S E S F L E N K S S V D D G N

241 ATA AAT TTA ACA GAT ACA AGT ACA TCA AAT AAA AGT TCT AAA AAA GGA CAT GGT AGA AGT
81 I N L T D T S T S N K S S K K G H G R S

301 AGA GTA AGA TCA GCA TCA GCT GCT GCA ATT CTT GAA GAA GAT GAT TCA AAA GAT GAT ATG
101 R V R S A S A A A I L E E D D S K D D M

361 GAA TTT AAA GCT TCT CCT TCA GTT GTT AAA ACA TCT ACT CCA TCA GGT ACA CAG ACA TCT
121 E F K A S P S V V K T S T P S G T Q T S

421 GGT TTA AAA TCA TCT AGT CCA TCT AGT ACA AAG TCA TCA AGT CCA TCA AAT GTA AAA TCA
141 G L K S S S P S S T K S S S P S N V K S

481 GCT AGT CCA CAT GGT GAA TCT AAT TCT TCT GAA GAA AGT ACT ACT AAA TCC TCA AAG AGA
161 A S P H G E S N S S E E S T T K S S K R

541 AGT GCT TCG GTT GCA GGT ATT GTA GGT GCC GAC GAA GAA GCA CCT CCT GCA CCA AAA AAC
181 S A S V A G I V G A D E E A P P A P K N

601 ACC CTC ACT CCA TTA GAA GAA TTA TAT CCT ACT AAT GTT AAT TTA TTT AAC TAT AAA TAT
201 T L T P L E E L Y P T N V N L F N Y K Y

661 TCA TTA AAC AAT ATG GAA GAA AAT ATC AAT ATA CTT AAA AAC GAA GGA GAT TTC GTT GCA
221 S L N N M E E N I N I L K N E G D L V A

721 CAA CCC GAA GAA TTT GAA TAT GAT GAA AAT ATG GAA AAA GCT AAA CAA GAC AAA AAA AAA
241 Q K E E F E Y D E N M E K A K Q D K K K

781 GCA CTT GAG AAA ATA GGA AAA CAA TCA GAC GAA GAA CCT TTT ATG TTT TCA GAA AAT AAA
261 A L E K I G K Q S D E E P F M F S E N K

841 TTT CTT GAA AAT CAA GTA AAA GAA AGA AAT GTT GCT GGA TCC TTT TCT CGA TTT TTC AGT
281 F L E N Q V K E R N V A G S F S R F F S

901 AAA TTA AAT CCT TTT AAG AAA GAT GAA GTA ATA GAA AAA ACT GAA GTA TCA AAG AAA ACA
301 K L N P F K K D E V I E K T E V S K K T

961 TTT TCA GGT ATA GGT TTT AAT CTT ACT GAC AAA GAA GCT AAA GTA TTA GGT GTA GGT GCA
321 F S G I G F N L T D K E A K Y L G V G A

1021 ACC TAT CAA GAA TAT CCA GAA ACC ATG TTA TAT AAC TGT CCA AAC AAT TCT AAT TTG TTT
341 T Y Q E Y P E T M L Y N C P N N S N L F

1081 GAT ACT ATA GAA TCA TTA CAA GGA AGA ATA ATT GAT ATT AAA AAA AGA GAA AGC ATG ATA
361 D T I E S L Q G R I I D I K K R E S M I

1141 TCA ACA ACT TTC GAA CAA CAA AAA GAA TGT TTA AAA AAT ATG GGT GTA CTT GAT CTT GAA
381 S T T F E Q Q K E C L K N M G V L D L E

FIG. 2A

1201 TTA AAC GAT ACA CAA TGT AAA TTT GGT ACA TGT ATA GGT AGC TTT GGA GAA CAT CAT CTT
401 L M D T Q C K F G T C I G S F G E M M L

1261 AGA TTA TAC GAA TTT GAG AAT GAC TTA TTT AAA TTT CAT CCA AAT ATT GAT TAT TTA ACT
421 R L Y E F E N D L F K F H P N I D Y L T

1321 TTA GCT GAT GGA TAT AAA TTA CAA AAA AAT CAT ATA TAT GAA TTA TCC CAT GTA AAC TTT
441 L A D G Y K L Q K N H I Y E L S W Y N F

1381 TGC TTA TTA AAT CCT AAA ACA TTA GAA GAA TTT TTA AAA AAA AAA GAA ATC AAG GAT CTT
461 C L L N P K T L E E F L K K K E I K D L

1441 ATG GGT GGT GAT GAT CTT ATA AAA TAT AAA GAA AAT TTT GAT AAC TTT ATG AGT ATA TCT
481 M G G D D L I K Y K E N F D N F M S I S

1501 ATA ACA TGC CAT ATT GAA TCT TTA ATA TAT GAT GAT ATT GAA GCA TCT CAA GAT ATT GCT
501 I T C H I E S L I Y D D I E A S Q D I A

1561 GCT GTA TTA AAA ATT GCT AAA AGT AAA TTA CAT GTA ATA ACA TCA GGT TTA TCA TAT AAA
521 A V L K I A K S K L H V I T S G L S Y K

1621 GCA AGA AAA TTA GTA TAT AAA ATT TAT AGT GAA ATT CAA AAA AAT CCA GAT GAA CTC TAT
541 A R K L V Y K I V S E I Q K N P D E L Y

1681 GAA AAA TTA ACA TGG ATT TAT GAT AAT ATC TAT ATG ATT AAA AGA TAT TAT ACT GCA TAT
561 E K L T W I Y D N I Y M I K R Y Y T A Y

1741 GCT TTA GAA GGT GTC TGT TCA TAT CTT GAA CAT GAT AAA AGT CAA ATC TAT ACA GAA TTA
581 A L E G V C S Y L E H D K S Q M Y T E L

1801 CAT ATT TAT AAC AAA ATA GTC GAC TCT GTT CGT TAT TAT AGT TCA TGC TTT AAA AAC GTT
601 H I Y N K I V D S V R Y Y S S C F K N V

1861 ATT GTT TAT AAT GCT ATC ATT TCT GGT ATA CAT GAA AAA ATA AAA CAT TTC TTA AAA TTA
621 I V Y N A I I S G I H E K I K H F L K L

1921 GTA CCA AGA CAC AAC TTT CTT TTG GAT TAT CAC TTT AAT TCA ATT TTT GAA AAA GAA ATT
641 V P R H N F L L D Y H F N S I F E K E I

1981 AAA CCA GCC AAA AAA TAT AGT ACT TCA CAT ATT TAT TTT GAT CCA ACT GTT GCA TCA TAT
661 K P A K K Y S T S H I Y F D P T V A S Y

2041 GCT TAT TAT AAT TTA GAT AGA AGA ACC ATG GTT ACT ATT ATT AAT GAT TAT TTC GAA GCA
681 A Y Y N L D R R T M V T I I N D Y F E A

2101 AAA AAA AAA GAA TTA ACC GTT ATA GTA TCT CGT ATG AAA ACA GAT ATG CTC AGT CTT CAA
701 K K K E L T V I V S R M K T D M L S L Q

2181 AAT GAA GAA TCA AAA ATA CCA AAT GAC AAA AGT GCA AAT TCA AAA CTA GCT ACA AGA TTA
721 N E E S K I P N D K S A N S K L A T R L

2241 ATG AAA AAA TTT AAA GCT GAA ATC AGA GAT TTC TTC AAA GAA ATG CGT ATA CAA TAT GCT
741 M K K F K A E I R D F F K E M R I Q Y A

2301 AAA TTA ATA AAC ATA CGT TAC AGA TCT CAC TTA AAG AAA AAC TAC TTT GCC TTC AAG AGA
761 K L I N I R Y R S H L K K N Y F A F K R

2361 TTA GAT TAAGAATATAAACTTGAAAAATATATATAATGTAAAAATATACTAAATATATTAATATATTAATATAATATATATATAT
781 L D

2438 ATATATATATATATATA

FIG. 2B

PLASMODIUM MEROZOITE RHOPTRIES ANTIGENIC POLYPEPTIDES

This is a division, of application Ser. No. 08/086,416 filed Jul. 1, 1993, now abandoned, which is a continuation of Ser. No. 07/992,988 filed Dec. 18, 1992, now abandoned, which is a continuation of Ser. No. 07/489,312 filed Mar. 5, 1990, now abandoned.

TECHNICAL FIELD

This application relates to antigenic polypeptides having at least one determinant immunologically cross-reactive with determinants on a polypeptide associated with the rhoptry organelles of the merozoite form of the malaria parasite Plasmodium falciparum. These antigenic polypeptides can be used to protect mammals against malaria.

BACKGROUND OF THE INVENTION

Malaria in human beings is caused by four species of Plasmodium, namely by *P. falciparum, P. vivax, P. ovale* and *P. malariae*. According to a report of the World Health Organisation (WHO) from the year 1986, there are worldwide almost 100 million cases of malaria infection. Of these about 1 million, mostly cases of young children which are infected with *P. falciparum,* are fatal. Because of the appearance of drug-resistant parasites and of insecticide-resistant mosquito vectors, malaria is spreading (Bruce-Chwatt, Essential Malariology, 2nd edition, Heinemann, London [1986]).

Recent technical advances have raised hopes that it would soon be possible to produce an antimalaria vaccine which would counteract the growing spread of malaria. Firstly, new methods in the development of malaria vaccines, e.g. the cloning of genes and their expression in microbial host organisms as well as the use of monoclonal antibodies for antigen identification, can be used. Secondly, long-term cultures of *P. falciparum* in human red blood cells (Trager et al., Science 193, 673–675 [1976]) have provided a ready source of material for the study of the malaria parasite. More recently, it has become possible to maintain all stages in the life cycle of the parasite in the laboratory (Ponnudurai et al., Trans. R. Soc. Trop. Med. Hyg. 76, 812–818 [1982]; Mazier et al., Science 22.7, 440–442 [1985]).

The natural life cycle of *P. falciparum* has three different stages. In the first stage, mosquitoes introduce sporozoites into the blood vessels of vertebrates during the intake of food. These sporozoites travel via the bloodstream to the liver and invade the hepatocytes of the host. In the second stage, merozoites develop from these sporozoites. These merozoites pass through several multiplication cycles in erythrocytes of the host and then develop to gametocytes. The gametocytes, which are the sexual stage of the parasite, are taken up by mosquitoes when they feed. After fertilization in the stomach of the insect the gametocytes develop into sporozoites which then travel to the salivary glands of the insect. From there the cycle can begin again.

Sporozoites, merozoites and gametocytes have different antigens (Scaife, Genetic Engineering 7, 57–90 [1988]). Vaccines can be produced in principle against any of the different stages of the malaria parasite. Various merozoite antigens have been used to induce immunity against malaria. None of these antigens has been found to be the ideal vaccine candidate. Here we present a novel schizont/merozoite antigen of the malaria parasite. This antigen is recognized by two monoclonal antibodies (MABs), MAB 2.13 and MAB 7.12, described by Hall et al. (Mol. Biochem. Parasitol. 7, 247–265 [1983]). MAB 2.13 strongly inhibits invasion of erythrocytes by malaria parasites. Western blot analysis (Towbin et al., Proc. Natl. Acad. Sci. USA 76, 4350–4354 [1979]) of protein extracts from whole parasites using MAB 2.13 revealed 4 major bands with a relative molecular mass of 65 kD, 70 kD, 78 kD and 80 kD, respectively, whereby 1 kD equals 1,000 daltons. Affinity purification of the protein extract from whole parasites followed by gelelectrophoretic analysis revealed two additional bands with a relative molecular mass of 40 kD and 42 kD. Most likely the natural form of the antigen recognized by MAB 2.13, the so-called 2.13 antigen, is the 80 kD species, whereas the other bands represent processed forms of this antigen. Whether the processed forms of the antigen occur also in nature, viz. in the parasite, is not clear. Immunofluorescence studies showed that the antigen recognized by MAB 2.13 is associated with the rhoptry organelles of Plasmodium merozoites. More specifically the MAB 2.13 recognizes a determinant or epitope on a polypeptide associated with the rhoptry organelles of Plasmodium merozoites. The rhoptries of Plasmodium are a pair of pear-shaped, electron-dense bodies situated at the apical end of the merozoite. Electron microscopic studies have implicated these organelles as having a key role in the invasion of erythrocytes by the parasite. It was found that by blocking the said determinant the MAB 2.13 is able to inhibit erythrocyte invasion. The other monoclonal antibody MAB 7.12 has similar properties to MAB 2.13 but does not block erythrocyte invasion as efficiently as MAB 2.13.

Campbell et al., Am. J. Trop. Med. Hyg. 33, 1051–1054 (1984) have described rhoptry-associated antigens of 78, 63, 42 and 40 kD present in protein extracts from the El Salvador and Malaysian strains of the *P. falciparum* parasite. Howard et al., Am. J. Trop. Med. Hyg. 33, 1055–1059 (1984) found proteins of 82, 70, 67, 39 and 37 kD in an immunoprecipitate from merozoites of a Vietnamese strain of *P. falciparum.* Schofield et al., Mol. Biochem. Parasitol. 18, 183–195 (1986) described four monoclonal antibodies recognizing antigens present in rhoptries of *P. falciparum* merozoites. Western blot analysis of a parasite extract using these antibodies yielded protein bands of 80, 66 and 42 kD. Two of the monoclonal antibodies described by Schofield et al. are capable of inhibiting the invasion of erythrocytes by merozoites in vitro. Clark et al. (Parasitol. Res. 73, 425–434 [1987]) have described two proteins having a molecular weight of 82,000 daltons and 65,000 daltons, respectively associated with the rhoptry organelles of *Plasmodium falciparum* merozoites. Braun-Breton et al. (Nature 332, 457–459 [1988]) have shown that cleavage of a phosphatidylinositol membrane anchor activates a serine protease associated with the soluble form of a *Plasmodium falciparum* membrane protein of a relative molecular mass of 76,000 dalton present in merozoite or isolated schizont membranes. In vitro experiments have shown that this serine protease appears to be involved in the process of red blood cell invasion by malaria merozoites and plays an important role in merozoite maturation. There is no experimental evidence, however, that the proteins described in the above references are in any way related to the protein recognized by previously described MAB 2.13 or 7.12. In addition, it is not known whether the proteins described in the above references are capable of inducing antibodies in a mammalian host which are capable of inhibiting the invasion of erythrocytes by the merozoite form of the malaria parasite in vivo. In contrast, Applicants have shown for the first time that the 2.13 antigen and, thus, the novel polypeptides of the present invention, are capable of inducing antibodies in a mammalian host which are capable of inhibiting the invasion of erythrocytes by the merozoite form of the malaria parasite in vivo.

SUMMARY OF THE INVENTION

This invention provides antigenic polypeptides having at least one determinant immunologically cross-reactive with determinants on a polypeptide associated with the rhoptry organelles of the merozoite form of the malaria parasite *Plasmodium falciparum.*

This invention also provides the DNA sequences or fragments thereof encoding the above antigenic polypeptides or fragments thereof; recombinant vectors containing and capable of directing the expression of such DNA sequences or fragments in compatible host organisms; and microorganisms containing such vectors which are capable of expressing the DNA sequences or fragments.

This invention further provides a method for producing an antigenic polypeptide having at least one determinant immunologically cross-reactive with one or more determinant on a polypeptide associated with the rhoptry organelles of 10 the merozoite form of the malaria parasite Plasmodium falciparum, which method comprises:

(a) culturing a host organism containing a recombinant vector which comprises a DNA sequence or fragment thereof encoding for the antigenic polypeptides or fragment thereof, under conditions in which the DNA sequence or fragment is expressed; and (b) isolating the antigenic polypeptide or fragment from the culture.

This invention still further provides immunologic compositions for protecting mammals against malaria.

This invention still further provides a method for protecting mammals against malaria, which method comprises administering an effective amount of the immunologic compositions of the invention to a mammal that is susceptible to malaria.

BRIEF DESCRIPTION OF THE FIGURES

FIG. 2A,B shows the nucleotide sequence (2) of the gene coding for the 2.13 antigen and the amino acid sequence (II) derived from the coding region.

DETAILED DESCRIPTION OF THE INVENTION

Figure 1:
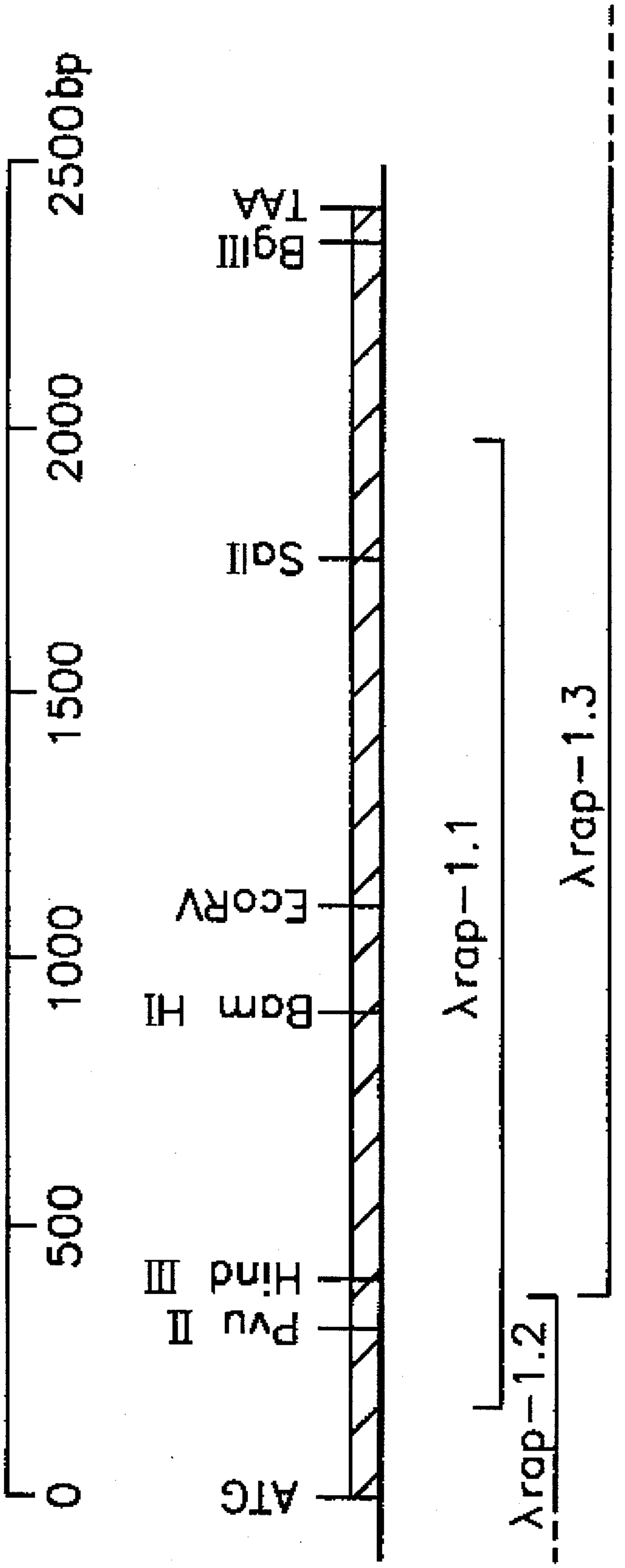
FIG. 1 shows a restriction map of the gene coding for the 2.13 antigen and the relative positions of the cloned fragments of the said gene in λ rap-1.1, λ rap-1.2 and λ rap-1.3.

Once the presence of an antigen is established by generating a MAB reacting specifically with said antigen, one is still far away from an unambiguous definition of the antigen per se, e.g. by the molecular weight of the natural form of the antigen and by its amino acid composition or preferably by its amino acid sequence. This is mostly due to the low abundance of these antigens in the parasite and thus to the difficulty to isolate sufficient amounts of the protein from the parasite allowing the characterization of the antigen. This has led to efforts to molecularly clone the gene encoding the protein recognized as antigen by the MABs 2.13 and 7.12. Although the art of genetic engineering is well advanced today it is still not straight-forward to clone a specific gene out of the multitude of genes present in an organism such as *Plasmodium falciparum*, especially when no probe consisting of an oligonucleotide sequence representing a short segment of the gene is available. When only a MAB is available an expression gene library of the parasite genome has first to be prepared, preferably a lambda phage expression gene library such as the one described in the Example (below) in which parasite DNA is expressed as a fusion polypeptides with β-galactosidase. The expression gene library is then screened for expression products reacting with MAB 2.13 and/or 7.12 and the DNA of a recombinant phage capable of expressing a polypeptide comprising the epitopes recognized by MAB 2.13 and/or 7.12 is isolated (Young et al., Proc. Natl. Acad. Sci. USA 80, 1194–1198 [1983]). The nucleotide sequence coding for the said polypeptide can be determined using methods well known in the art. An example of such a nucleotide sequence is the nucleotide sequence (1):

AAGATGAATTTTCAAGTGAATCCTTTTTAGAAAATAAATCTAGTGTTGATGATGGAAATA

TAAATTTAACAGATACAAGTACATCAAATAAAAGTTCTAAAAAAGGACATGGTAGAAGTA

GAGTAAGATCAGCATCAGCTGCTGCAATTCTTGAAGAAGATGATTCAAAAGATGATATGG

AATTTAAAGCTTCTCCTTCAGTTGTTAAAACATCTACTCCATCAGGTACACAGACATCTG

GTTTAAAATCATCTAGTCCATCTAGTACAAAGTCATCAAGTCCATCAAATGTAAAATCAG

CTAGTCCACATGGTGAATCTAATTCTTCTGAAGAAAGTACTACTAAATCCTCAAAGAGAA

GTGCTTCGGTTGCAGGTATTGTAGGTGCCGACGAAGAAGCACCTCCTGCACCAAAAAACA

CCCTCACTCCATTAGAAGAATTATATCCTACTAATGTTAATTTATTTAACTATAAATATT

CATTAAACAATATGGAAGAAAATATCAATATACTTAAAAACGAAGGAGATTTAGTTGCAC

AAAAAGAAGAATTTGAATATGATGAAAATATGGAAAAAGCTAAACAAGACAAAAAAAAAG

CACTTGAGAAAATAGGAAAACAATCAGACGAAGAACCTTTTATGTTTTCAGAAAATAAAT

TTCTTGAAAATCAAGTAAAAGAAAGAAATGTTGCTGGATCCTTTTCTCGATTTTTCAGTA

AATTAAATCCTTTTAAGAAAGATGAAGTAATAGAAAAAACTGAAGTATCAAAGAAAACAT

-continued

TTTCAGGTATAGGTTTTAATCTTACTGACAAAGAAGCTAAAGTATTAGGTGTAGGTGCAA

CCTATCAAGAATATCCAGAAACCATGTTATATAACTGTCCAAACAATTCTAATTTGTTTG

ATACTATAGAATCATTACAAGGAAGAATAATTGATATTAAAAAAAGAGAAAGCATGATAT

CAACAACTTTCGAACAACAAAAAGAATGTTTAAAAAATATGGGTGTACTTGATCTTGAAT

TAAACGATACACAATGTAAATTTGGTACATGTATAGGTAGCTTTGGAGAACATCATCTTA

GATTATACGAATTTGAGAATGACTTATTTAAATTTCATCCAAATATTGATTATTTAACTT

TAGCTGATGGATATAAATTACAAAAAAATCATATATATGAATTATCCCATGTAAACTTTT

GCTTATTAAATCCTAAAACATTAGAAGAATTTTTAAAAAAAAAAGAAATCAAGGATCTTA

TGGGTGGTGATGATCTTATAAAATATAAAGAAAATTTTGATAACTTTATGAGTATATCTA

TAACATGCCATATTGAATCTTTAATATATGATGATATTGAAGCATCTCAAGATATTGCTG

CTGTATTAAAAATTGCTAAAAGTAAATTACATGTAATAACATCAGGTTTATCATATAAAG

CAAGAAAATTAGTATATAAAATTTATAGTGAAATTCAAAAAAATCCAGATGAACTCTATG

AAAAATTAACATGGATTTATGATAATATCTATATGATTAAAAGATATTATACTGCATATG

CTTTAGAAGGTGTCTGTTCATATCTTGAACATGATAAAAGTCAAATGTATACAGAATTAC

ATATTTATAACAAAATAGTCGACTCTGTTCGTTATTATAGTTCATGCTTTAAAAACGTTA

TTGTTTATAATGCTATCATTTCTGGTATACATGAAAAAATAAAACATTTCTTAAAATTAG

TACCAAGACACAACTTTCTTTTGGATTATCACTTT

This nucleotide sequence represents a partial nucleotide sequence of the gene coding for the 2.13 antigen, which gene has the nucleotide sequence (2):

ATGAGTTTCTATTTGGGTAGCTTAGTAATAATATTCCATGTACTCTTCCGTAATGTCGCT

GATGGTATAAATGTAAACGGAGATAATAATTATGGGAAAACAATAATCAATAATGATTTC

AATTTTGATGATTACAATTATTGGACACCAATAAATAAAAAGGAATTTTTAAATTCCTAT

GAAGATGAATTTTCAAGTGAATCCTTTTTAGAAAATAAATCTAGTGTTGATGATGGAAAT

ATAAATTTAACAGATACAAGTACATCAAATAAAAGTTCTAAAAAAGGACATGGTAGAAGT

AGAGTAAGATCAGCATCAGCTGCTGCAATTCTTGAAGAAGATGATTCAAAAGATGATATG

GAATTTAAAGCTTCTCCTTCAGTTGTTAAAACATCTACTCCATCAGGTACACAGACATCT

GGTTTAAAATCATCTAGTCCATCTAGTACAAAGTCATCAAGTCCATCAAATGTAAAATCA

GCTAGTCCACATGGTGAATCTAATTCTTCTGAAGAAAGTACTACTAAATCCTCAAAGAGA

AGTGCTTCGGTTGCAGGTATTGTAGGTGCCGACGAAGAAGCACCTCCTGCACCAAAAAAC

ACCCTCACTCCATTAGAAGAATTATATCCTACTAATGTTAATTTATTTAACTATAAATAT

TCATTAAACAATATGGAAGAAAATATCAATATACTTAAAAACGAAGGAGATTTAGTTGCA

CAAAAAGAAGAATTTGAATATGATGAAAATATGGAAAAAGCTAAACAAGACAAAAAAAAA

GCACTTGAGAAAATAGGAAAACAATCAGACGAAGAACCTTTTATGTTTTCAGAAAATAAA

TTTCTTGAAAATCAAGTAAAAGAAAGAAATGTTGCTGGATCCTTTTCTCGATTTTTCAGT

AAATTAAATCCTTTTAAGAAAGATGAAGTAATAGAAAAAACTGAAGTATCAAAGAAAACA

TTTTCAGGTATAGGTTTTAATCTTACTGACAAAGAAGCTAAAGTATTAGGTGTAGGTGCA

ACCTATCAAGAATATCCAGAAACCATGTTATATAACTGTCCAAACAATTCTAATTTGTTT

GATACTATAGAATCATTACAAGGAAGAATAATTGATATTAAAAAAAGAGAAAGCATGATA

TCAACAACTTTCGAACAACAAAAAGAATGTTTAAAAAATATGGGTGTACTTGATCTTGAA

-continued

TTAAACGATACACAATGTAAATTTGGTACATGTATAGGTAGCTTTGGAGAACATCATCTT

AGATTATACGAATTTGAGAATGACTTATTTAAATTTCATCCAAATATTGATTATTTAACT

TTAGCTGATGGATATAAATTACAAAAAAATCATATATATGAATTATCCCATGTAAACTTT

TGCTTATTAAATCCTAAAACATTAGAAGAATTTTTAAAAAAAAAAGAAATCAAGGATCTT

ATGGGTGGTGATGATCTTATAAAATATAAAGAAAATTTTGATAACTTTATGAGTATATCT

ATAACATGCCATATTGAATCTTTAATATATGATGATATTGAAGCATCTCAAGATATTGCT

GCTGTATTAAAAATTGCTAAAAGTAAATTACATGTAATAACATCAGGTTTATCATATAAA

GCAAGAAAATTAGTATATAAAATTTATAGTGAAATTCAAAAAAATCCAGATGAACTCTAT

GAAAAATTAACATGGATTTATGATAATATCTATATGATTAAAAGATATTATACTGCATAT

GCTTTAGAAGGTGTCTGTTCATATCTTGAACATGATAAAAGTCAAATGTATACAGAATTA

CATATTTATAACAAAATAGTCGACTCTGTTCGTTATTATAGTTCATGCTTTAAAAACGTT

ATTGTTTATAATGCTATCATTTCTGGTATACATGAAAAAATAAAACATTTCTTAAAATTA

GTACCAAGACACAACTTTCTTTTGGATTATCACTTTAATTCAATTTTTGAAAAAGAAATT

AAACCAGCCAAAAAATATAGTACTTCACATATTTATTTTGATCCAACTGTTGCATCATAT

GCTTATTATAATTTAGATAGAAGAACCATGGTTACTATTATTAATGATTATTTCGAAGCA

AAAAAAAAAGAATTAACCGTTATAGTATCTCGTATGAAAACAGATATGCTCAGTCTTCAA

AATGAAGAATCAAAAATACCAAATGACAAAAGTGCAAATTCAAAACTAGCTACAAGATTA

ATGAAAAAATTTAAAGCTGAAATCAGAGATTTCTTCAAAGAAATGCGTATACAATATGCT

AAATTAATAAACATACGTTACAGATCTCACTTAAAGAAAAACTACTTTGCCTTCAAGAGA

TTAGATTAA

Using the genetic code it was found that in the nucleotide sequence (1) two reading frames were interrupted by several stop codons and thus most likely do not code for a *P. falciparum* polypeptide. The third reading frame starting with nucleotides 3 to 5, viz. GAT as first codon encoding the amino acid aspartic acid (abbreviated "D" in accordance with the single-letter system described by Dayhoff, in "Atlas of Protein Sequence and Structure", National Biomedical Research Foundation, Washington D.C., 1972) is open and codes for a polypeptide having the amino acid sequence (I)

D E F S S E S F L E N K S S V D D G N I N L T D T S T S N K S

S K K G H G R S R V R S A S A A A I L E E D D S K D D M E F K

A S P S V V K T S T P S G T Q T S G L K S S S P S S T K S S S

P S N V K S A S P H G E S N S S E E S T T K S S K R S A S V A

G I V G A D E E A P P A P K N T L T P L E E L Y P T N V N L F

N Y K Y S L N N M E E N I N I L K N E G D L V A Q K E E F E Y

D E N M E K A K Q D K K K A L E K I G K Q S D E E P F M F S E

N K F L E N Q V K E R N V A G S F S R F F S K L N P F K K D E

V I E K T E V S K K T F S G I G F N L T D K E A K V L G V G A

T Y Q E Y P E T M L Y N C P N N S N L F D T I E S L Q G R I I

D I K K R E S M I S T T F E Q Q K E C L K N M G V L D L E L N

-continued

D T Q C K F G T C I G S F G E H H L R L Y E F E N D L F K F H

P N I D Y L T L A D G Y K L Q K N H I Y E L S H V N F C L L N

P K T L E E F L K K K E I K D L M G G D D L I K Y K E N F D N

F M S I S I T C H I E S L I Y D D I E A S Q D I A A V L K I A

K S K L H V I T S G L S Y K A R K L V Y K I Y S E I Q K N P D

E L Y E K L T W I Y D N I Y M I K R Y Y T A Y A L E G V C S Y

L E H D K S Q M Y T E L H I Y N K I V D S V R Y Y S S C F K N

V I V Y N A I I S G I H E K I K H F L K L V P R H N F L L D Y

H F

The amino acid sequence (I) codes for a polypeptide containing 591 amino acid residues. If the natural form of the *P. falciparum* antigen recognized by MABs 2.13 and 7.12, viz. the 2.13 antigen, has indeed a molecular weight of 80,000 Dalton, the amino acid sequence (I) represents about three quarters of the amino acid sequence of the said antigen. Due to the method used to clone the DNA coding for the amino acid sequence (I) the said amino acid sequence must comprise the antigenic determinant (that is the epitope) recognized by MAB 2.13. The antigenic determinant is formed by a specific molecular configuration of one or more sub-sequences in the amino acid sequence of the 2.13 antigen or the polypeptide comprising the amino acid sequence (I) or a partial sequence thereof, which partial sequence comprises the sub-sequence recognized by MAB 2.13.

The nucleotide sequence (2) codes for a polypeptide containing 782 amino acid residues and having the following amino acid sequence (II):

M S F Y L G S L V I I F H V L F R N V A D G I N V N G D N N Y

G K T I I N N D F N F D D Y N Y W T P I N K K E F L N S Y E D

E F S S E S F L E N K S S V D D G N I N L T D T S T S N K S S

K K G H G R S R V R S A S A A A I L E E D D S K D D M E F K A

S P S V V K T S T P S G T Q T S G L K S S S P S S T K S S S P

S N V K S A S P H G E S N S S E E S T T K S S K R S A S V A G

I V G A D E E A P P A P K N T L T P L E E L Y P T N V N L F N

Y K Y S L N N M E E N I N I L K N E G D L V A Q K E E F E Y D

E N M E K A K Q D K K K A L E K I G K Q S D E E P F M F S E N

K F L E N Q V K E R N V A G S F S R F F S K L N P F K K D E V

I E K T E V S K K T F S G I G F N L T D K E A K V L G V G A T

Y Q E Y P E T M L Y N C P N N S N L F D T I E S L Q G R I I D

I K K R E S M I S T T F E Q Q K E C L K N M G V L D L E L N D

T Q C K F G T C I G S F G E H H L R L Y E F E N D L F K F H P

-continued

N I D Y L T L A D G Y K L Q K N H I Y E L S H V N F C L L N P

K T L E E F L K K K E I K D L M G G D D L I K Y K E N F D N F

M S I S I T C H I E S L I Y D D I E A S Q D I A A V L K I A K

S K L H V I T S G L S Y K A R K L V Y K I Y S E I Q K N P D E

L Y E K L T W I Y D N I Y M I K R Y Y T A Y A L E G V C S Y L

E H D K S Q M Y T E L H I Y N K I V D S V R Y Y S S C F K N V

I V Y N A I I S G I H E K I K H F L K L V P R H N F L L D Y H

F N S I F E K E I K P A K K Y S T S H I Y F D P T V A S Y A Y

Y N L D R R T M V T I I N D Y F E A K K K E L T V I V S R M K

T D M L S L Q N E E S K I P N D K S A N S K L A T R L M K K F

K A E I R D F F K E M R I Q Y A K L I N I R Y R S H L K K N Y

F A F K R L D.

The calculated molecular weight of this polypeptide is in good agreement with the apparent molecular weight determined for the *P. falciparum* antigen recognized by the MABs 2.13 and 7.12, i.e. 80,000 Dalton.

Since the present invention provides the amino acid sequence of the 2.13 antigen it has now become possible to prepare large amounts of polypeptides comprising the amino acid sequence (II) or partial sequences thereof comprising the amino acid sequence forming the antigenic determinant recognized by MAB 2.13 such as e.g. the amino acid sequence (I). These polypeptides can be prepared in substantially pure form i.e. free from contaminating malaria parasite derived materials.

In addition to the sub-sequences recognized by MAB 2.13 the amino acid sequence (II) may comprise other antigenic determinants which are immunologically cross-reactive with determinants on the 2.13 antigen of the rhoptry organelles of Plasmodium merozoites. The said determinants on the 2.13 antigen may be defined by labelling the 2.13 antigen in merozoites, e.g. by using the lactoperoxidase labelling method (Hogg, Proc. Natl. Acad. Sci. USA 71, 489–492 [1974]) or by some other method known in the art and determining the amino acid residues labelled. Peptides comprising the amino acid residues determined in this way may be used as vaccines in accordance with the method disclosed in European Patent No. 44710.

The detailed three-dimensional structure of the 2.13 antigen or of a sub-sequence thereof forming an antigenic surface determinant may be defined by computer-assisted X-ray or NMR analysis. Based on the structural information obtained in this way novel polypeptides comprising a sub-sequence forming about the same three-dimensional structure and thus mimicking an antigenic determinant may be designed (for a review see Blundell et al., Nature 326, 347–352 [1987]). The said novel polypeptides may have an amino acid sequence which is different from the amino acid sequence of the 2.13 antigen or the sub-sequences thereof forming the antigenic surface determinant mentioned above. Some of the amino acid residues of the said novel polypeptide may also be modified in order to stabilize the three-dimensional configuration of the sub-sequence forming the antigenic determinant. Since the said sub-sequence in the novel polypeptide has about the same three-dimensional structure as the antigenic determinant on the 2.13 antigen the novel polypeptide immunologically cross-reacts with the determinant present on the 2.13 antigen.

Thus, the present invention is directed to antigenic polypeptides having at least one determinant immunologically cross-reactive with determinants on the *Plasmodium falciparum* polypeptide associated with the rhoptry organelles of the merozoite form of the malaria parasite which *Plasmodium falciparum* polypeptide has the amino acid sequence (II). In order to be useful as a malaria vaccine, the determinants on the *Plasmodium falciparum* polypeptide associated with the rhoptry organelles of the merozoites have to be accessible for an immune reaction of mammals against the malaria parasite. The invention is also directed to a polypeptide comprising the amino acid sequence (II) or a partial sequence thereof such as the amino acid sequence (I), which polypeptide immunologically cross-reacts with determinants on the *Plasmodium falciparum* polypeptide defined above. An example for a polypeptide of the present invention is the Plasmodium merozoite antigen associated with the rhoptry organelles of Plasmodium merozoites having a relative molecular mass of approximately 80kD which antigen is recognized by MABs 2.13 and 7.12. The preferred polypeptides are capable of inducing antibodies in a mammalian host, which antibodies are capable of inhibiting the invasion of erythrocytes by the merozoite form of the malaria parasite in vivo. The polypeptides may be in unglycosylated form or may be glycosylated. Other posttranslational modifications are possible such as covalently attaching a glycosylphosphatidyl inositol moiety. The polypeptide may also be an anti-idiotypic antibody or a fragment thereof having an antigenic determinant which is immunologically cross-reactive with the surface determinants mentioned above. An anti-idiotypic antibody is an antibody directed against the binding site of an antibody directed against a given antigenic determinant and thus the antigenic site of the said anti-idiotypic antibody has a similar molecular configuration as the antigenic determinant (Linthicum et al., BioEssays 3, 213–217 [1985]). Preferably the polypeptides of the present invention are in substantially pure form.

The invention relates also to polypeptides having an amino acid sequence derived from the amino acid sequences indicated above by additions, deletions, insertions or amino acid substitutions, provided that these polypeptides are still cross-reactive with determinants of the polypeptide associated with the rhoptry organelles of Plasmodium merozoites comprising the amino acid sequence (I). The invention is also concerned with DNAs coding for a polypeptide in accordance with the invention and with recombinant vectors containing such a DNA, especially expression vectors, i.e. recombinant vectors, in which the DNA which codes for a polypeptide in accordance with the present invention is bound to an expression control sequence in such a way that the polypeptide which is encoded by the DNA can be expressed. The preferred DNA comprises the nucleotide sequence (2) or a partial sequence thereof such as the nucleotide sequence (1). Moreover, the present invention is concerned with unicellular host organisms which contain such a recombinant vector or an expression vector and with a process for the production of such organisms. Furthermore, the present invention is concerned with a process for the production of the polypeptides and with the use of these polypeptides for the immunization of mammals against malaria.

As certain substitutions in the amino acid sequence of a polypeptide have little or no influence on the tertiary structure or the biological activity of the polypeptide, the amino acid sequence of the polypeptides in accordance with the invention can differ from the amino acid sequences given above. Examples of such amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu and vice versa (see Doolittle, in "The Proteins", Eds. Neurath, H, and Hill, R. L., Academic Press, New York [1979]).

The polypeptides in accordance with the invention can be covalently bound to a carrier material or can be adsorbed thereon. Suitable carrier materials are natural or synthetic polymeric compounds such as e.g. copolymers of one or more amino acids (e.g. polylysine) or sugars (e.g. polysaccharides). Other suitable carrier materials are natural polypeptides such as hemocyanins (e.g. KLH=keyhole limpet hemocyanin), serum proteins (e.g. gammaglobulin, serum albumin) and toxoids (e.g. diphtheria or tetanus toxoid). Other suitable carrier materials are known to the person skilled in the art.

The covalent bonding of the polypeptides in accordance with the invention to the carrier materials can be effected in a known manner, e.g. directly by the formation of a peptide or ester bond between free carboxyl, amino or hydroxyl groups of the polypeptide and the corresponding groups on the carrier material or indirectly by using conventional, bifunctional reagents such as e.g. m-maleimidobenzoyl-N-hydroxysuccinimide ester (MBS) or succinimidyl 4-(p-maleimidophenyl)butyrate (SMPB). These and other bifunctional reagents are commercially obtainable, e.g. from Pierce Chemical Company, Rockford, Ill., U.S.A. Further, $C_{2-7}$-dialkanals, such as e.g. glutaraldehyde (Avrameas, Immunochem. 6, 43–52 [1969]), can be used. The carrier material having the polypeptides bonded thereon can be separated from non-bonded polypeptides and, if desired, from excess reagents by known methods (e.g. dialysis or column chromatography).

The peptides of the present invention can be produced by conventional methods of peptide synthesis in the liquid phase or, preferably, on the solid phase, such as the methods of Merrifield (J. Am. Chem. Soc. 85, 2149–2154 [1963]) or by other equivalent methods of the state of the art.

The solid phase synthesis begins with the C-terminal amino acid of the peptide to be synthesized, which is coupled in protected form to an appropriate resin. The starting material can be produced by coupling an amino acid, which is protected at the amino group, to a chloromethylated or a hydroxymethylated resin via a benzyl ester bridge or via an amide bond to a benzhydrylamine (BHA) resin, a methylbenzhydrylamine (MBHA) resin or a benzyloxybenzyl alcohol resin. These resins are commercially obtainable and their production and use are well-known.

General methods for the protection and removal of protecting groups from amino acids, which can be used in this invention, are described in "The Peptides", Vol. 2 (edited by E. Gross and J. Meienhofer, Academic Press, New York, 1–284 [1979]). Protecting groups include e.g. the 9-fluorenylmethyloxycarbonyl (Fmoc), the tertiary butyloxycarbonyl (Boc), the benzyl (Bzl), the t-butyl (But), the 2-chlorobenzyloxycarbonyl (2Cl-Z), the dichlorobenzyl (Dcb) and the 3,4-dimethylbenzyl (Dmb) group.

After removal of the α-amino protecting group the protected amino acids are coupled stepwise in the desired sequence to the C-terminal amino acid bonded to the resin. The complete peptide can thus be synthesized. As an alternative thereto, small peptides can be synthesized and can then be joined together to give the desired peptide. Suitable coupling reagents belong to the state of the art, with dicyclohexylcarbodiimide (DCC) being especially preferred.

Each protected amino acid or peptide is added in excess to the solid phase synthesis reaction vessel and the coupling reaction can be carried out in dimethylformamide (DMF) or methylene chloride ($CH_2Cl_2$) or a mixture of both. In cases of incomplete coupling, the coupling reaction is repeated before the N-terminal α-amino protecting group is removed for the purpose of coupling the next amino acid. The yield of each coupling step can be followed, preferably according to the ninhydrin method. The coupling reactions and the washing steps can be carried out automatically. The cleavage of the peptide from the carrier material can be achieved by methods which are well-known in peptide chemistry, e.g. by reaction with hydrogen fluoride (HF) in the presence of p-cresol and dimethyl sulphide for 1 hour at 0° C., followed possibly by a second reaction with HF in the presence of p-cresol for 2 hours at 0° C. The cleavage of the peptides from chloromethylated or hydroxymethylated carrier materials gives peptides having a free C-terminus; the cleavage of peptides from benzylhydrylamine or methylbenzylhydrylamine carriers gives peptides having an amidated C-terminus.

Alternatively, the polypeptides of the present invention can also be produced using methods well known in the art of recombinant DNA technology (Maniatis et al. in "Molecular Cloning—A Laboratory Manual", Cold Spring Harbor Laboratory [1982]). Thereby a DNA which codes for such a polypeptide can be synthesized by conventional chemical methods, e.g. by the phosphotriester method which is described by Narang et al. in Meth. Enyzmol. 68, 90–108 [1979], or by the phosphodiester method (Brown et al., Meth. Enzymol. 68, 109–151 [1979]). In both methods long oligonucleotides are first synthesized and then joined together in a predetermined way. The nucleotide sequence of the DNA can be partially or fully identical to the nucleotide sequence which codes for the natural polypeptide in the rhoptry organelles of Plasmodium merozoites. Since the genetic code is degenerate, there exists on the other hand the possibility that a partially or completely different nucleotide sequence codes for the same polypeptide. The codons selected can be adapted to the preferred codon usage of the host used to express the recombinant polypeptide (Grosjean et al., Gene 18, 199–209 [1982]). Care must be taken that the DNA thus-obtained does not contain partial sequences which make the construction of the expression vector difficult, e.g. by introducing an undesired restriction enzyme cleavage site, or which prevents the expression of the polypeptide.

A DNA coding for a polypeptide of the present invention is obtained by cloning parasite DNA into an expression phage vector, e.g. into the λ phage vector gt11 which is obtainable from the American Type Culture Collection (ATCC), 12301 Parklawn Drive, Rockville, Md., USA. These phage vectors are transfected into suitable host cells, e.g. into *E. coli* Y1088 containing the plasmid pMC9 (available e.g. from ATCC). The expression gene library obtained in this way is then screened using polyclonal or monoclonal antibodies as described by Young et al., Proc. Natl. Acad. Sci. USA 80, 1194–1198 [1983] and in the Example infra.

Preferably the DNA is obtained by cleaving DNA of a Plasmodium parasite strain with one or more restriction endonucleases and cloning the fragments into a suitable vector according to procedures well known in the art (Maniatis et al., supra). The parasite DNA library is then screened with a suitable probe. Such suitable probes are oligonucleotides which correspond to a partial sequence of the DNA coding for the 2.13 antigen or the DNA having the nucleotide sequence (1). The manner in which these probes are selected and used is known to the person skilled in the art. Examples of such probes are oligonucleotides having the sequence TTGGTGCAGGAGGTGCT or AAGCTACCTATACATGT. Clones containing a DNA insert hybridizing to the probe are grown up and the DNA is isolated. Subsequently, the DNA fragment can be inserted into a suitable vector, preferably into a vector which provides the necessary expression signals. Examples of such expression vectors are described in European Patent Application, Publication No. 186 069 which was published on 2nd Jul. 1986. The polypeptides of the present invention can, after corresponding adaptation of the nucleotide sequence, also be produced using other suitable expression vectors known to the person skilled in the art.

The recombinant vector which contains a DNA coding for a polypeptide in accordance with the invention is subsequently introduced into a suitable unicellular host organism. Suitable unicellular host organisms are prokaryotic or eukaryotic cells. Examples for prokaryotic cells are microorganisms, e.g. bacterial cells, such as *E. coli* cells or *B. subtilis* cells, which are capable of expressing polypeptides encoded by the recombinant expression vectors. A large number of eukaryotic cells suitable as unicellular host organisms for recombinant vectors are known to the person skilled in the art. Examples for such eukaryotic cells are yeast cells (e.g. *Saccharomyces cerevisiae*) and cultured cells of higher eukaryotes, such as insect cells (e.g. using the baculovirus vector system; for a review see Doerfler, Curr. Top. Microbiol. Immunol. 131, 51–68 [1986] or Yong Kang, Adv. in Virus Research 35, 177–192 [1988]) and vertebrate cells (for a review see Rigby, Genetic Engineering, Vol. 3, R. Williamson, ed., Academic Press, New York, pp. 83–141 [1982]). The preferred unicellular host organism is *E. coli* M15 (described as DZ291 by Villarejo et al. in J. Bacteriol. 120, 466–474 [1974]). Other suitable host organisms are *E. coli* 294, *E. coli* RR1 and *E. coli* W3110 (all available from ATCC and other sources). Depending on the host organism used the polypeptide may be in glycosylated form.

The manner in which the expression of the polypeptides in accordance with the invention is effected depends on the recombinant expression vector and on the host organism used. In the case of bacteria and yeast the host organisms which contain the recombinant expression vector are grown up under conditions which are optimal for the growth of the host organism. Towards the end of the exponential growth, when the increase in the number of cells per unit time decreases, the expression of the polypeptide of the present invention is induced, i.e. the DNA coding for the polypeptide is transcribed and the transcribed mRNA is translated. The induction can be effected by adding an inducer or a derepressor to the growth medium or by altering a physical parameter, e.g. by a temperature change. In the recombinant expression vector used in the present invention the expression is controlled by the lac repressor. By adding isopropyl-β-D-thiogalactopyranoside (IPTG) the expression control sequence is derepressed and thereby the synthesis of the polypeptide is induced.

The polypeptide produced in the unicellular host organisms can be secreted by special transport mechanisms or can be isolated by breaking open the unicellular organism. The host organism can be broken open by mechanical (Charm et al., Meth. Enzymol. 22, 476–556 [1971]), enzymatic (lysozyme treatment) or chemical (e.g. detergent treatment, urea or guanidine.HCl treatment) means or by a combination thereof.

In eukaryotes, polypeptides which are secreted from the cells are synthesized in the form of a precursor molecule. The mature polypeptide results by cleavage of the so-called signal peptide. As prokaryotic host organisms are not capable of cleaving eukaryotic signal peptides from precursor molecules, eukaryotic polypeptides must be expressed directly in their mature form in prokaryotic host organisms. The translation start signal AUG, which corresponds to the codon ATG on the level of the DNA, causes all polypeptides synthesized in a prokaryotic host organism to have a methionine residue at the N-terminus. In certain expression systems this N-terminal methionine residue is cleaved off. It has, however, been found that the presence or absence of the N-terminal methionine has often no influence on the biological activity of a polypeptide (see Winnacker, in "Gene und Klone", p. 255, Verlag Chemie, Weinheim, BRD [1985]). In cases where the N-terminal methionine is troublesome, it can also be cleaved off by means of peptidases which are specific for the N-terminal methionine. Miller et al., Proc. Natl. Acad. Sci. U.S.A. 84, 2718–2722 [1987], have described the isolation of such a peptidase from Salmonella typhimurium. The present invention is accordingly concerned with polypeptides with or without a N-terminal methionine residue.

The polypeptides in accordance with the present invention can be purified by known methods such as, for example, by centrifugation at different velocities, by precipitation with ammonium sulfate, by dialysis (at normal pressure or at reduced pressure), by preparative isoelectric focusing, by preparative gel electrophoresis or by various chromatographic methods such as gel filtration, high performance liquid chromatography (HPLC), ion exchange chromatography, reverse phase chromatography and affinity chromatography (e.g. on Sepharose™ Blue CL-6B, on phosphocellulose, on carrier-bound monoclonal antibodies directed against the polypeptide or on metal chelate resins such as those described in European Patent Application, Publication No. 253 303.

The preferred purification method in the present invention is affinity chromatographic purification. The purification of the polypeptides in accordance with the invention on carrier-bound monoclonal antibodies 2.13 and 7.12 is especially preferred.

The polypeptides of the present invention can be present in the form of multimers, e.g. in the form of dimers, trimers or tetramers. The subunits of these multimers may be linked together by covalent or noncovalent bonds. Multimers often result when polypeptides are produced in prokaryotic host organisms, for example by the formation of disulfide bridges between cysteine residues.

The polypeptides of the present invention can also be prepared in the form of fusion polypeptides. In that case, a polypeptide of the present invention is covalently linked via a peptide bond to one or more fusion partners which typically are peptides or polypeptides. Preferably, the fusion partner peptides or polypeptides improve the properties of the fusion polypeptide in comparison to those of the polypeptide without the fusion partner. Suitable fusion partners are polypeptides having an antigenic determinant or determinants immunologically cross-reactive with other antigens of the malaria parasite, preferably antigens from another stage of the malaria parasite, thereby improving the efficacy of vaccines containing said fusion polypeptide. Several such antigens are known (see review of Scaife, supra). Antigens from the sporozoite stage such as the circumsporozoite (CS) protein or other polypeptides comprising repeat sequences such as the tetrapeptide repeat Asn-Ala-Asn-Pro present in the *P. falciparum* CS protein are preferred. The fusion partner may also be a T cell epitope such as one of those described by Good et al. (Science 235, 1059–1062 [1987]). Alternatively the fusion partner may also be an affinity peptide and thereby contribute to the ease of recovery of the fusion polypeptide.

An example of a suitable fusion partner is an affinity peptide which binds preferably to an affinity chromatography carrier material. Examples of such affinity peptides are peptides containing at least two histidine residues. Such affinity peptides bind selectively to nitrilotriacetic acid-nickel chelate resins (see e.g. European Patent Application, Publ. No. 253 303).

Fusion polypeptides which contain such an affinity peptide can therefore be separated selectively from the remaining polypeptides by means of such resins. Fusion proteins can be produced by conventional peptide synthesis methods or by genetic engineering whereby DNA fragments which code for a polypeptide of the present invention are linked with one or more DNA fragments which code for said fusion partner. Preferably, the fusion polypeptides are prepared by genetic engineering, e.g. by introducing a DNA coding for a polypeptide according to the present invention into an expression vector which comprises the necessary expression control sequences and a DNA coding for said fusion partner.

The polypeptides of the present invention may be used diagnostically to detect antibodies directed against the determinant of the polypeptide associated with the rhoptry organelles of Plasmodium merozoites having the amino acid sequence (I) according to methods well known in the art.

The present invention is also directed to immunogenic compositions which contain a polypeptide in accordance with the present invention as well as a suitable adjuvant. Examples for suitable adjuvants are aluminium hydroxide and aluminium phosphate. Other suitable adjuvants or delivery systems (e.g. *Salmonella typhimurium* or Vaccinia virus) for use in human beings and animals are known to the person skilled in the art (WHO Techn. Rep. Series 595, 1–40 [1987]; Warren et al., Ann. Rev. Immunol. 4, 369–388 [1986]; Morein, Nature 332, 287–288 [1988]; Klausner, BIO/TECHNOLOGY 6, 773–777 [1988] and Bromford, Parasitology Today 5, 41–46 [1989]). The polypeptides or immunogenic compositions in accordance with the invention can be present as lyophilizates for reconstitution with sterile water or a salt solution, preferably phosphate buffered saline.

By introducing the polypeptides and immunogenic compositions in accordance with the invention into mammals, their immune system is activated, that is, the production of antibodies against the polypeptide is induced. The present invention is also concerned with such antibodies. The antibodies in accordance with the invention recognize the natural equivalent of the polypeptide in the malaria parasite and can therefore be used therapeutically for blocking red blood cell invasion by the merozoites, for passive immunization or for diagnostic purposes.

Antibodies against the polypeptides in accordance with the invention can be produced in monkeys, rabbits, horses, goats, guinea pigs, rats, mice, cows, sheep, etc, and also in human beings. The antiserum or the purified antibody can be used as required. The antibodies can be purified in a known manner, for example, by precipitation with ammonium sulfate. It is also possible to produce monoclonal antibodies which are directed against the polypeptide of the present invention in accordance with the method developed by K.hler et al. (Nature, 256, 495–497 [1975]). Polyclonal or monoclonal antibodies can also be used for the affinity-chromatographic purification of the polypeptides of the present invention or of their natural equivalent, the 2.13 antigen.

The polypeptides and immunogenic compositions in accordance with the invention can be used as vaccines for the immunization of mammals against malaria. Thereby the immune system of a mammal, preferably a human, is stimulated with an immunizing amount of said polypeptide or immunogenic composition. The mode of administration, the dosage, as well as the number of injections can be optimized in a manner known to the person skilled in the art. Typically, several injections are administered over a long time period in order to obtain a high titer of antibodies against the malaria antigen, for example, against a polypeptide according to the present invention.

Having now generally described this invention, the same may be more readily understood by reference to the following Example. It should be understood that the Example is for illustrative purposes only and should not be construed as limiting this invention in any way to the specific embodiment recited therein. For the sake of clarity, the Example is preceded by a list of abbreviations, a list of buffers and media and a collection of general methods used in the Example.

| Abbreviations: | |
|---|---|
| ATP | adenosine triphosphate |

-continued

| Abbreviations: | |
|---|---|
| bp | base pair |
| BCIP | 5-bromo-4-chloro-3-indolyl phosphate |
| BSA | bovine serum albumin |
| cpm | impulse per minute |
| dATP | deoxyadenosine triphosphate |
| dCTP | deoxycytidine triphosphate |
| dGTP | deoxyguanosine triphosphate |
| dTTP | deoxythymidine triphosphate |
| DTT | dithiothreitol |
| EDTA | ethylenediaminetetraacetic acid |
| EGTA | ethylene glycol bis(2-aminoethyl ether)-N,N,N',N'-tetraacetic acid |
| HEPES | [4-(2-hydroxyethyl)-1-piperazineethanesulfonic acid] |
| IPTG | isopropyl-β-D-thiogalactopyranoside |
| kb | 1,000 base pairs |
| kD | kilodalton (=1,000 Dalton) |
| M | molar |
| mM | millimolar |
| ml | milliliter |
| nm | nanometer |
| NBT | nitro blue tetrazolium |
| PFU | plaque-forming units |
| PMSF | phenylmethylsulfonyl fluoride |
| RPM | revolutions per minute |
| SDS | sodium dodecylsulfate |
| TEMED | N,N,N',N'-tetramethylethylenediamine |
| Tris | tris(hydroxymethyl)aminomethane |
| X-Gal | 5-bromo-4-chloro-3-indolyl-β-D-galactoside |

Buffers and media:

100× Denhardt's (100 ml):
- 2 g polyvinylpyrrolidone
- 2 g Ficoll (Pharmacia, Uppsala, Sweden)
- 2 g BSA
- 100 mg sodium azide DNA gel loading buffer
- 1× TBE (see below for composition)
- 20% glycerol
- 0.1% bromophenol blue
- 0.1% xylenecyanol Formamide mix:
- 80% (w/v) formamide
- 50 mM Tris/boric acid [pH 8.3]
- 1 mM EDTA
- 0.1% xylenexyanol
- 0.1% bromophenol blue HIN buffer:
- 10 mM Tris/HCl [pH 7.4]
- 10 mM magnesium chloride
- 50 mM sodium chloride Ligase buffer:
- 50 mM Tris/HCl [pH 7.8]
- 10 mM magnesium chloride
- 20 mM DTT
- 10 mM dATP LS buffer:
- 440 mM HEPES [pH 6.6]
- 110 mM Tris/HCl [pH 8.0]
- 11 mM magnesium chloride
- 22 mM β-mercaptoethanol
- 44 μM dATP
- 44 μM dTTP
- 44 μM dGTP

- 11 O.D.$_{260}$ units of random hexanucleotides (Pharmacia)

LB medium: per liter:
- 10 g Bactotrypton
- 5 g yeast extract
- 10 g sodium chloride SDS gel loading buffer:
- 5% SDS
- 5mM Tris/HCl [pH 6.8]
- 200 mM DTT
- 20% glycerol
- 0.1% bromophenol blue 20× SSC: per liter:
- 175.3 g sodium chloride
- 82.2 g sodium citrate [pH 7.0]

SM buffer:
- 10 mM sodium chloride
- 10 mM magnesium chloride
- 10 mM Tris/HCl [pH 7.4]

10×T4 polymerase buffer:
- 0.33M Tris/acetate [pH 7,9]
- 0.66M potassium acetate
- 0.10M magnesium acetate
- 5 mM DTT
- 1 mg/ml BSA 10× TBE
- 0.89M Tris/boric acid [pH 8.0]
- 0.89M boric acid
- 20 mM EDTA 10× TBS:
- 0.5M Tris/HCl [pH 7.4]
- 1.5M sodium chloride 100× TE:
- 1M Tris/HCl [pH 8.0]
- 100 mM EDTA BBL medium: per liter:
- 10 g trypticase (BBL, Division of Becton Dickinson and Co., Cockeysville, Md., USA)
- 5 g sodium chloride Alkaline phosphatase buffer:
- 100mM Tris/HCl [pH 9.5]
- 100mM sodium chloride
- 5 mM magnesium chloride High salt buffer:
- 50mM Tris/HCl [pH 7.5]
- 10mM magnesium chloride
- 100mM sodium chloride Medium salt buffer:
- 10 mM Tris/HCl [pH 7.5]
- 10mM magnesium chloride
- 10mM sodium chloride Core buffer
- 50mM Tris/HCl [pH 8.0]
- 10mM magnesium chloride
- 50mM sodium chloride TES buffer:
- 20mM Tris/HCl [pH 7.5]
- 10mM sodium chloride
- 0.1mM EDTA TM buffer:

40mM Tris/HCl [pH 7.5]

10mM magnesium chloride

50mM sodium chloride

Phage buffer: per liter:

3g potassium dihydrogen phosphate

7g disodium hydrogen phosphate

5g sodium chloride

0.095g magnesium sulfate

0.011g calcium sulfate

0.01g gelatine

General methods:

Method 1: DNA precipitation with lithium acetate

The DNA solution is treated with a tenth by volume of 5 lithium acetate and two volumes of isopropanol, mixed well and placed on dry ice for 10 minutes. The precipitated DNA is centrifuged for 10 minutes at 12,000 RPM (20° C.) in an Eppendorf bench centrifuge and the supernatant is carefully removed. The sediment is washed once with 80% (v/v) ethanol and subsequently dried for 5 minutes in a vacuum centrifuge. The DNA is dissolved in water and processed further.

Method 2: Agarose gel electrophoresis of DNA

The dried DNA is dissolved in 1× DNA gel loading buffer and heated to 65° C. for 5 minutes. 100 ml of 1×TBE buffer are mixed with agarose (800 mg for a 0.8% gel or 1.2 g for a 1.2% gel) and boiled until the agarose has dissolved completely. After cooling 2 μl of ethidium bromide solution (10 mg/ml) are added and the gel solution is poured into a horizontal gel electrophoresis apparatus. After solidification of the gel the samples are applied to the gel and the DNA is separated for 2 hours at 150 volt constant voltage. Commercial standard mixtures of DNA fragments of defined length are used as size markers. The DNA bands are visualized under 300 nm UV light.

Method 3: Isolation of DNA from an agarose gel

The DNA is separated on an agarose gel (Methode 2). A trough is cut in front of the band to be purified and a piece of dialysis tubing inserted at the end of the trough. The trough is filled with 1× TBE buffer and the DNA electroeluted onto the dialysis tubing at 200 V for 10 to 15 minutes. It is then back-eluted into the trough for 45 seconds. The DNA solution is extracted twice with water-saturated isobutanol, twice with phenol/chloroform/isoamyl alcohol (25:24:1) and is then precipitated by the addition of 1/10th volume 3M sodium acetate pH 5.2 and 2 volumes ethanol. After standing at −70° C. for 15 minutes the precipitate is pelleted at 12,000 g for 10 minutes, dried and resuspended in 1× TE buffer.

Method 4: Plaque purification of lambda phages

A bacterial culture (e.g. *E. coli* Y1088 available e.g. from ATCC) is infected on an agar plate (Maniatis et al., supra, pp. 70–71) with lambda phages. Thereby, lytic plaques are formed in the lawn of bacteria. An agar cylinder (diameter 5 mm) containing a plaque is cut from the agar with a inverted Pasteur pipette. The agar cylinder is transferred into an Eppendorf test tube containing 500 μl of SM buffer and the test tube is shaken for 5 minutes. The phage suspension is centrifuged (5 minutes at 12,000 RPM, 20° C.) and the supernatant is transferred into a fresh test tube. 1 μl of the phage suspension is diluted with 1 ml of SM buffer. 1, 10 and 100 μl of this solution are added to 50 μl of a cell suspension of *E. coli* Y1090 cells containing the plasmid pMC9 (available e.g. from ATCC) which had been $Mg^{++}$-treated in accordance with Morrison, (Methods Enzymol. 68, 326–331 [1979]). After a 30 minutes incubation at room temperature the solution is added to 3 ml of 0.8% (w/v) agar in LB medium and the mixture is poured onto LB-ampicillin agar plates (LB medium, 40 μg/ml ampicillin). Depending on the titre, some plates (e.g. those with the 1:1,000 dilution) have individual plaques which, when they are positive in the antibody reaction or the DNA hybridization, can be isolated. The phages from the plaques can be grown up and e.g. used for the isolation of phage DNA.

Method 5: Preparation of plate lysate phage stock

An appropriate number of plaque forming units (e.g. 10000) is used to infect 100 μl of plating cells (methode 5) and these are plated on to a freshly prepared BBL plate and grown a 37° C. overnight. The top agar, which should exhibit confluent lysis, is then scraped into 5 ml phage buffer and allowed to stand for 2 hours at room temperature. The top agar is finally pelleted at 4,000 g for 10 minutes and the supernatant retained as phage stock.

Method 6: Preparation of plating cells for lambda phage infection

An individual colony of the *E. coli* strain to be used (e.g. Y1090 available e.g. from ATCC) is inoculated into 5 ml LB medium and grown overnight at 37° C. The suspension is then diluted 50-fold and grown at 37° C. for a further 2 hours before pelleting the cells at 4,000 g for 10 minutes at 4° C. and resuspending the cells in 1/10th volume of ice cold 10 mM magnesium sulfate. The cells may be stored at 4° C. for up to 2 weeks. The cells are used for generating phage lambda plaques as follows. An appropriate number of plaque forming phage units is added to 100 μl of plating cells. The suspension is left at room temperature for 20 minutes, then 3 ml of liquid BBL top agar (at 45° C.) is added and the mixture poured on to an 80 mm bottom agar plate.

Method 7: Transformation of *E. coli*

3 ml LB medium is inoculated with *E. coli* cells and shaken at 37° C. overnight. 1 ml of this saturated culture is used to inoculate 50 ml LB medium. The culture is shaken until the optical density at 600 nm ($OD_{600}$) has reached a value of 0.2. The cells are sedimented (5 minutes at 6,000 RPM, room temperature) and resuspended in 25 ml of ice-cold 100 mM magnesium chloride. The cells are again centrifuged off (see above) and suspended in 5 ml of 100 mM calcium chloride. The competent cells are left at 4° C. for at least 30 minutes. For the transformation 10 μl of DNA solution containing 1 to 10 ng DNA are added to 100 μl of competent cells and incubated first for 20 minutes on ice, then at 42° C. for 2 minutes and finally again on ice for 20 minutes.

When using vectors of the M13 type (Yanisch-Perron et al., Gene 33, 103–119 [1985]), there are now added 50 μl of 10% (w/v) X-Gal in dimethylformamide, 10 μl of 100 mM IPTG in water and 50 μl of a saturated *E. coli* TG-1 culture (*E. coli* TG-1 is available from Amersham, Little Chalfont, England; alternatively *E. coli* JM 101 available from ATCC or *E. coli* JM 103 can be used). After mixing well 3 ml of 0.8% (w/v) agar in BBL medium are added and the mixture is poured on to a BBL agar plate. The agar plates are then incubated at 37° C. overnight.

When using plasmid DNA, which can be selectionized for antibiotic resistance 1 ml of LB medium is added to the transformation mixture and the incubation is carried out at 37° C. for one hour. The cells are centrifuged off for 3 minutes at 6,000 RPM (room temperature) and resuspended in 100 μl of LB medium. These 100 μl are distributed uniformly on a LB agar plate which contains the antibiotic required for the selection and likewise incubated at 37° C. overnight.

Method 8: Preparation of the DNA for sequencing

*E. coli* strains TG-1, JM 101 or JM 103 can be used as hosts for cloning vectors of the M13 type for sequencing DNA according to Messing, Meth. Enzymol. 101, 20–78 [1983]. When a vector of the M13 type, which vector comprises a DNA fragment to be sequenced, is transformed into one of the mentioned host cells, then white plaques result. These white plaques are picked with a toothpick and resuspended in 3 ml of LB medium. A further 60 μl of a saturated host culture are added and the mixture is shaken at 37° C. for 6 hours. 1.5 ml of culture are transferred into an Eppendorf test tube and centrifuged (5 minutes at 12,000 RPM, 20° C.). 1.2 ml of supernatant are transferred into a new test tube and mixed with 300 μl of 20% (w/v) polyethylene glycol, 2.5M sodium chloride solution and incubated at room temperature for 20 minutes. The remainder of the culture is stored at 4° C. or used for the preparation of "mini-lysate" DNA (Method 10). The phages are precipitated by centrifugation (10 minutes at 12,000 RPM, 20° C.). The sediment is dissolved in 100 μl of 1× TES buffer and extracted with 100 μl of saturated phenol. The phases are separated by centrifugation (5 minutes at 12,000 RPM). 80 μl of the aqueous phase are transferred into a new reagent test tube, the DNA is precipitated (Method 1) and dissolved in 12 μl of water.

Method 9: DNA sequencing

1 μl of the DNA prepared according to Method 8 are mixed with 6 μl of water, 2 μl of 1× TM buffer, and 1 μl of oligonucleotide primer and heated at 65° C. for 2 minutes. Thereafter, the solution is allowed to cool slowly to 35° C. In the meanwhile, 4 test tubes each containing 2"μl of the stop solutions $A^o$, $G^o$, $T^o$ and $C^o$ are prepared. The stop solutions have the following composition:

$A^o$: 1 pM ddATP, 100 μM dCTP, 100 μM dGTP, 100 μM dTTP $C^o$: 160 μM ddCTP, 12.5 μM dCTP, 125 μM dGTP, 125 μM dTTP $G^o$: 250 μM ddGTP, 125 μM dCTP, 12.5 μM dGTP, 125 μM dTTP $T^o$: 400 μM ddTTP, 100 μM dCTP, 100 μM dGTP, 25 μM dTTP.

1.5 units of Klenow polymerase (Pharmacia), 0.5 μl of [$^{35}$S]-dATP (6000 Ci/mmol), 0.8 μl 10.1M DTT, 1.6 μl 1× TM buffer and 4.8 μl $H_2O$ are pipetted into the test tubes containing the DNA and mixed well. In each case 4 μl of this solution are mixed with the stop solution and incubated at 30° C. for 20 minutes. 2 μl of 0.25 mM dATP is added to each of the four test tubes, mixed and again incubated for 20 minutes. Finally, the reaction is stopped by adding 2 μl of formamide mix and heating to 80° C. for 3 minutes. The DNA is now applied to a 0.4 mm gel of the following composition:

34 ml $H_2O$ 3 ml 10× TBE-buffer 28.8 g urea 3.6 g acrylamide 180 mg bisacrylamide 360 μl 10% ammonium persulfate 50 μl TEMED The DNA is separated for 1 to 6 hours by electrophoresis at 40 watt constant output. The glass plates are separated and the gel is fixed for 5 minutes in 10% (v/v) acetic acid and 10% (v/v) methanol. The gel is then washed twice with 10% (v/v) methanol for 5 minutes, mounted on Whatman 3M paper (Whatman Ltd., Maidstone, England) and dried in a gel dryer. The dried gel is autoradiographed for 20 hours using X-ray Film (e.g. KODAK-XAR, Eastman Kodak Co., Rochester, N.Y., USA).

Method 10: DNA isolation on a small scale ("mini-lysate")

About 1 to 2 ml of bacterial culture (e.g.*E. coli* TG-1 containing a vector of the M13 type; see Method 8) are centrifuged for 5 minutes at 12,000 RPM (20° C.). The supernatant is carefully sucked off. The sedimented cells are resuspended in 500 μl of 50 mM Tris/HCl [pH 7.6], 5 mM EDTA. After the addition of a small spatula tip of lysozyme the suspension is incubated at room temperature for 5 minutes. 15 μl of 25% (w/v) lithium dodecylsulfate solution and 30 μl of 5M potassium acetate are then added and the suspension is mixed carefully. After incubation on ice for 15 minutes the sample is centrifuged for 15 minutes at 12,000 RPM (4° C.). The supernatant is decanted into a new test tube and treated with 50 μl of RNase solution (10 mg/ml). After incubation at 37° C. for 5 minutes the sample is extracted once with phenol and once with chloroform (in each case the same volumes). The DNA in the aqueous phase is precipitated (Method 1) and finally dissolved in 100 μl of water.

Method 11: Radioactive labelling of DNA "oligo-labelling"

The DNA to be labelled (up to 100 ng) is diluted to 7 μl volume with $H_2O$, heated to 95° C. for 2 minutes and quick cooled on ice. After adding 5 μl of α-[$^{32}$P]dCTP (3,000 Ci/mmol), 12 μl of LS buffer and 3 units of Klenow Polymerase (Maniatis et al., supra, pp 113–114) the reaction is incubated for 4 to 16 hours at room temperature. The labelled DNA may be used directly for hybridisations. Immediately prior to its use in hybridisations the DNA must be heated to 95° C. for 10 minutes.

Method 12: Hybridisation of DNA

The filter containing DNA is incubated for 1 hour at 65° C. in 0.5M sodium phosphate buffer [pH 7], 7% SDS. To this is added approximately $10^7$ cpm of radioactive sample (method 11). After incubation at 65° C. overnight the filters are washed twice for 30 minutes in 0.2×SSC, 0.1% SDS at 65° C. The filters are dried and exposed against X-ray film (e.g. Kodak XAR).

Method 13: Preparation of a 10% SDS polyacrylamide gel according to Laemmli, Nature 227, 680–685 [1970]

60 ml separating gel 15 ml 1.5M Tris/HCl [pH 8.8], 0.4% (w/v) SDS, 8 mM EDTA.

20 ml 29% (w/v) acrylamide, 1% (w/v) bisacrylamide in water 29 ml water.

500 μl 1 10% (w/v) ammonium persulfate in water.

The solutions are mixed. Immediately before pouring between 2 glass plates 100 μl of TEMED are added. After the separating gel has polymerized the collecting gel having the following composition is poured in:

20 ml collecting gel:

5 ml 0.5M Tris/HCl [pH 6.8], 0.4% (w/v) SDS, 8 mM EDTA.

3 ml 29% (w/v) acrylamide, 1% (w/v) bisacrylamide in water.

12 ml water.

250 μl 1 10% (w/v) ammonium persulfate in water.

The solutions are mixed, 30 μl TEMED are added and poured onto the separating gel. A probe comb is inserted prior to the polymerization. 190 mM glycine, 25 mM Tris [pH 7.6], 1% (w/v) SDS is used as the electrophoresis buffer. Commercial molecular weight standards can be used as size markers.

Method 14; Immunoblots (Western blot)

Up to 100 μl of a protein sample are separated on a 12% SDS polyacrylamide gel overnight at 100 V constant voltage. The gel is removed and placed in transfer buffer. A sheet of nitrocellulose filter paper is moistened with water and placed on the gel. Gel and nitrocellulose sheet are covered with Whatman 3MM paper and then a sponge is placed on each of them. The sandwich which is thus obtained is then introduced into an electrophoresis apparatus, whereby the nitrocellulose sheet is directed towards the positive pole. The transfer of the proteins is effected by electrophoresis at 300 mA constant current for 2 hours. After the transfer the nitrocellulose sheet is shaken for 10 minutes in 1× TBS buffer. Subsequently, it is pre-incubated for 30 minutes in 1× TBS, 5% (w/v) skimmed milk powder. An antibody directed against the protein to be detected is diluted in the ratio 1:1,000 in 1× TBS, 5% (w/v) skimmed milk powder and incubated for one hour with the nitrocellulose sheet. Thereafter, the sheet is washed five times for three minutes in fresh 1× TBS and subsequently incubated for one hour with alkaline phosphatase-conjugated goat-anti-rabbit IgG-Fc-fragments (Promega Biotech Corp., Madison, Wis., USA) which were diluted 1:7,500 in 1× TBS containing 5% (w/v) skimmed milk powder. The nitrocellulose sheet is again washed as above and subsequently placed in 5 ml of alkaline phosphatase buffer containing 33 μl of NBT and 16.5 μl BCIP (50 mg/ml each in dimethylformamide) and mixed well. After the bands have been made visible the nitrocellulose sheet is stored in water in order to prevent an overexposure. Pre-stained marker proteins can be used as molecular weight markers.

Method 15 Southern transfer of DNA on to nylon membranes

About 10 μg of plasmid or parasite DNA per slot are separated by electrophoresis on an agarose gel (Method 2). The gel is first photographed and then incubated for 15 minutes in 0.5M sodium hydroxide, 1.5M sodium chloride solution. After that the gel is neutralized by incubating it twice for 15 minutes in 0.02M sodium hydroxide, 1M ammonium acetate and then placed on a clean glass plate. A nylon membrane (Hybond N, available from Amersham) is placed on the gel, followed by three sheets of Whatman 3MM and about 20 papertowels. The assembly is weighed down from above with a 500 g weight. After 3 hours the membrane is removed and dried at room temperature. The dried membrane is exposed to U.V. light, face-down on a transilluminator for 5 minutes and may then be treated further in accordance with Method 12.

EXAMPLE

Construction Of The Expression Gene Bank Of *P. falciparum*

*P. falciparum* cells (K1 isolate) were grown in 10 culture dishes as described by Trager et al., Science 193, 673–675 [1976] and subsequently washed in culture medium containing 0.1% saponin. The washed parasites were resuspended in 2 ml of 10 mM EDTA [pH 8.0], 0.5% (w/v) SDS. After the addition of 50 mg of proteinase K the mixture was incubated at 65° C. for 10 minutes and subsequently treated with 2 ml of phenol (saturated with Tris/HCl [pH 8.0]). The phases were mixed by shaking and again separated by centrifugation (10 minutes at 6,000 RPM, 20° C.). The phenol extraction was repeated twice (an interphase should no longer be visible). The DNA was precipitated according to Method 1, washed with ethanol and dried. The DNA was dissolved in 2 ml of water and sheared mechanically, i.e. by squeezing the DNA solution 80 times through a syringe with a 0.5×16 mm needle. Thereafter, 0.2 volumes of 5×EcoRl methylase buffer (50 mM Tris/HCl [pH 7.5], 0.25M NaCl, 50 mM EDTA, 25 mM β-mercaptoethanol, 0.4 mM S-adenosylmethionine) were added. 10 μg of DNA were methylated at 37° C. for 30 minutes with 50 units of EcoR1 methylase (New England Biolabs, Beverly, Mass., USA). The DNA was extracted once with phenol as described above and precipitated in accordance with Method 1. The DNA was dissolved in 200 μl of T4 polymerase buffer and, after the addition of 5 μl of 5 mM dATP, dCTP, dGTP and dTTP as well as 10 units of T4 polymerase, incubated at 37° C. for 30 minutes. The DNA was again extracted with phenol and precipitated in accordance with Method 1. The DNA was dissolved in 50 μl of ligase buffer. After the addition of 0.01 $OD_{260}$-units of phosphorylated EcoRI oligonucleotide adaptors (New England Biolabs) and 2 μl of T4-DNA ligase (12 Weiss units, New England Biolabs) the adaptors were ligated to the DNA at 14° C. overnight. The DNA was precipitated according to Method 1, dissolved in 20 μl of 1× DNA gel loading buffer and separated on a 0.8% agarose gel (Method 2). DNA fragments having a length of 2 to 6 kb were isolated in accordance with Method 3. The DNA obtained was dissolved in 50 μl of water and, after the addition of 6 μl of 10×ligase buffer, 2 μl of dephosphorylated lambda arms (Promega Biotech Corp.) and 6 Weiss units of T4-DNA ligase, ligated at 14° C. overnight. The DNA was precipitated (Method 1) and dissolved in 5 μl of water. After the addition of 20 μl of "Packaging Extract" (Genofit, S. A., Geneva, Switzerland) the DNA was packed in phage particles at 20° C. for 2 hours according to the directions of the manufacturer. After the addition of 500 μl of SM buffer as well as 50 μl of chloroform the gene bank was ready for the antibody test.

Antibody Test Of The Gene Bank

The monoclonal antibodies 2.13 and 7.12 were produced as described by Hall et al. (supra). These MABs recognize polypeptides of 80–65 kD in Western blots.

*E. coli* cells strain Y1090 were incubated in 3 ml of LB medium at 37° C. overnight. On the next morning the cells were diluted 50-fold in LB medium and grown for 2 hours at 37° C. They were then sedimented (10 minutes at 7,000 g, 20° C.) and resuspended in 5 ml 10 mM magnesium sulfate. Thirty batches of $10^4$ phage particles from the gene bank were added to 100 μl of this cell suspension and incubation was carried out at room temperature for 30 minutes. 3 ml of 0.8% agar solution in BBL medium, warmed to 42° C., were added to each batch and mixed well. The soft agar having the infected cells was distributed on BBL agar plates (diameter 82 mm). The agar plates were then incubated at 42° C. for 3,5 hours. A nitrocellulose filter, which had first been immersed in 100 mM IPTG solution and dried, was placed on each dish and incubation was carried out at 37° C. for 3 hours. The position of the filter relative to the dish was marked. The filters were incubated for 30 minutes in 1× TBS, 5% skimmed milk powder containing 0.01% Antifoam A (Sigma, St. Louis, Mo., USA). Monoclonal antibody ascitic fluid containing MAB 2.13 was diluted 1:1,000 with 1× TBS/5% (w/v) milk powder. The filters were incubated in the presence of said MAB ascitic fluid at room temperature for 30 minutes and then washed once for 5 minutes in 1× TBS, twice for 5 minutes in 1× TBS, 0.05% Nonidet P40 (Sigma) and once again in 1× TBS for 5 minutes. This was followed by an incubation for 30 minutes with a 1:7,500 dilution of alkaline phosphatase conjugated goat anti-mouse IgG (Promega Biotech Corp.) in 1× TBS, 5% (w/v) milk powder. The filters were again washed as above and the filters developed colorimetrically at room temperature using 5 ml of alkaline phosphatase buffer containing 33 μl 1NBT and 16.5 μl 1BCIP (P+S Biochemicals, England; catalogue No. P3771). Plaques which were positive were identified and picked from the Petri dishes on the basis of the markings. The phages in the individual plaques were plated out in soft agar in different dilutions according to Method 4 and positive plaques were again identified as described above. An individual, positive plaque λrap1.1 was picked, grown up according to Grossberger, Nucleic Acids Res. 15, 6737 [1987] and the DNA was isolated.

Detection Of The Recombinant Protein Expressed By λ2.13

The clone λrap1.1 was plaque purified (Method 4) and a plate lysate phage stock was prepared (Method 5). The cloned phage λrap1.1 was then lysogenised into *E. coli* strain Y1090 as follows. To 10 μl of Y1090 plating cells (Method 6),was added $10^6$ plaque forming units of the phage λrap1.1. LB medium (200 μl 1) was added and the mixture left for 3 hours at 30° C. The suspension was then streaked out on to an LB plate and grown overnight at 30° C. Colonies were isolated and picked on to replica plates, one grown at 30° C. and the other grown at 42° C. Those colonies which grew at 30° C. but not at 42° C. were assumed to be lysogens of λrap1.1.

A lysogen of λrap1.1 was grown overnight at 30° C. in 5 ml LB medium. It was then diluted 10-fold with LB medium and grown for 3 hours at 30° C. Synthesis of the fusion protein was induced by adding IPTG to a final concentration 100 μM and moving the culture to 42° C. After 30 minutes 3 ml of this culture was pelleted at 12,000 g for minutes and resuspended in 100 μl of SDS-PAGE loading buffer. The sample was boiled for 5 minutes and then loaded on to a 10% SDS-polyacrylamide gel (Method 13) and run at a constant voltage of 100 V overnight. The sample was then blotted on to nitrocellulose paper and immunologically detected using antisera (Method 14). Both polyclonal serum against β-galactosidase and the monoclonal antibody 2.13 recognized a broad band showing the presence of a fusion protein with an apparent molecular weight of 150–170 kD. A polyclonal serum raised against the purified antigen also recognized these bands very strongly.

Analysis And Sequencing Of The Cloned DNA Insert

The λrap1.1 DNA (2 μg) was dissolved in high salt buffer (20 μl), digested at 37° C. for 1 hour with 11 units EcoRI and analysed on a 0.8% agarose gel (Method 2). No insert was observed. The λrap1.1 DNA (2 μg) was then dissolved in high salt buffer (20 μl) and digested at 37° C. for 1 hour with 10 units MluI. A 3.9 kb DNA fragment was observed by agarose gel electrophoresis (Method 2) indicating a cloned insert of 1.7 kb. A further digestion of λrap1.1 DNA (2 μg) in high salt buffer (20 μl ) with 11 units EcoRI and 10 units MluI at 37° C. for 1 hour yielded a DNA fragment of 3.4 kb suggesting that the EcoRI site at the 5' end of the insert is retained but the EcoRI site at the 3' end of the insert is lost.

The λrap1.1 DNA (2 μg) was then digested in core buffer (20 μl ) with 11 units EcoRI for 1 hour at 37° C. The enzyme was heat inactivated by a 10 minutes incubation at 65° C. After adding 16 μl water, 2 μl 140 mM β-mercaptoethanol and 2 μl 10.2% Triton™ X-100 the DNA was further digested by adding 20 units KpnI. The reaction mixture was incubated at 37° C. for 1 hour and the enzyme then heat inactivated at 65° C. for 10 minutes. An EcoRI/KpnI fragment of 2.7 kb was observed by agarose gel electrophoresis (Method 2). For sequencing this fragment was ligated into the sequencing vectors M13 mp18 and M13 mp19 (e.g. available from New England BioLabs, Beverly, Mass., USA). This was done by digesting 2 μg of each vector with EcoRI and KpnI as described for λrap1.1 above. The digested vectors M13 mp18 and M13 mp19 (40 ng) were each added to the EcoRI/KpnI digested λrap1.1 DNA (100 ng) in 20 μl ligase buffer with 1 unit T4 DNA ligase and incubated at 15° C. overnight. Competent TG-1 cells were transformed with the ligated DNA (Method 7). White plaques were isolated, amplified and sufficient DNA for the sequence determination was prepared (Method 8). A minilysate preparation of RF DNA (Messing, supra; see also Method 10) from the M13 mp18 subclone (0.5 μg) was dissolved in 20 μl of Medium salt buffer and digested with 3 units HindIII. Similarly this DNA was also digested with BamHI. Both digests showed the presence of a HindIII site and a BamHI site in the cloned DNA insert. The DNA sequence of the insert was determined according to Method 9 using the information obtained from a restriction enzyme analysis of the DNA. The insert had the nucleotide sequence (1) shown above.

Method Of Obtaining The Full Gene Encoding The 2.13 Antigen

Approximately 60% of the gene encoding for the 2.13 antigen is already comprised in λrap1.1. The following method was used to obtain the full gene encoding the 2.13 antigen. DNA (5 μg) from the subclone of M13 mp18 containing the KpnI/EcoRI fragment of λrap1.1 was taken up in 20 μl of high salt buffer and treated with the restriction enzymes EcoRI (10 units) and SalI (10 units) for 1 hour at 37° C. The DNA was analysed by agarose gel electrophoresis (Method 2) and a 1.7 kb fragment was isolated (Method 3). Some of this DNA (100 ng) was radioactively labelled (Method 11) and hybridised (Method 12) to a Southern blot (Method 15) of *P. falciparum* (K1 strain) DNA (3 μg) which has been digested with HindIII (3 units) in 20 μl medium salt buffer at 37° C. for 1 hour. Two DNA fragments of about 3 kb and 11 kb were observed. These two DNA fragments were also present in the gene bank of Kl DNA HindIII fragments present in the vector λNM1149 (Goman et al., Mol. Biochem. Parasitol. 5, 391–400 [1982]). By screening this gene bank using the SalI/EcoRI fragment mentioned above DNAs containing the remainder of the gene were obtained (any other gene bank of *P. falciparum* could be used for this purpose). The location of these fragments and their relation to the parasite gene appears in FIG. 1. They were sequenced by the dideoxynucleotide chain termination method after subcloning into the appropriate M13 vectors. Instability of some of the sub-fragments made it necessary to use several synthetic oligonucleotide primers to complete the sequence. The entire sequence of the gene appears in FIG. 2.

The coding sequence reveals a number of points of interest in the structure of the 2.13 antigen. At its N-terminus it has a putative signal peptide sequence (see arrow in FIG. 2A), suggesting that this antigen is directed through the endoplasmic reticulum and the Golgi apparatus to its point of destination. The 2.13 antigen has no transmembrane domains or oligopeptide repeats. The most interesting features are sequences which could form positively-charged amphiphilic α-helices (underlined in FIG. 2A, B). Such structures could be used by the protein to penetrate the membrane of the erythrocyte during invasion by the merozoite.

It is said in the introductory part of the specification that Braun-Breton et al. have defined a rhoptry antigen which behaves on polyacrylamide gels similarly to 2.13 antigen. It is believed to be protective to Saimiri monkeys and is thought to be a serine protease activated by phospholiphase C, suggesting that it is attached to the membrane by a glycosylphosphoinositol (GPI) linker. Inspection of the amino acid sequence of the 2.13 antigen shows that none of the motifs conserved in serine protease is present, nor does it have a potential target for attachment of a GPI linker. We conclude, therefor, that the rhoptry antigen of Braun-Breton et al. is different from 2.13 antigen.

Purification Of The Antigen Recognized By Monoclonal Antibody 2.13

Purified monoclonal antibody 2.13 was coupled to cyanogen bromide activated Sepharose™ 4B (Pharmacia) using the method recommended by the manufacturer. Cell pellets from bulk cultures of *P. falciparum* were harvested and extracted with at least 5 volumes of 1% (w/v) Nonidet P40, 2% (w/v) sodium deoxycholate, 500 mM Tris/HCl (pH 8.0), 5 mM EDTA, 5 mM EGTA, 5 mM iodoacetamide, 0.2 mM PMSF and 10 µg/ml each of pepstatin, chymostatin, antipain, leupeptin, at 4° C. for 1 hour. Fresh PMSF was added to 0.2 mM and the extract centrifuged at 100,000 g for 3 hours at 4° C. The supernatant had fresh PMSF added to 0.2 mM and was passed through a 10 ml column of Sepharose™ 4B-bound MAB 2.13 equilibrated with 1% (w/v) Nonidet P40, 2% (w/v) sodium deoxycholate, 50 mM Tris/HCl (pH 8.0), 5 mM EDTA, 5 mM EGTA. The Sepharose™ 4B-bound MAB 2.13 column was then washed with at least 5 volumes of wash buffer (1% Nonidet P40, 0.5% (w/v) sodium deoxycholate, 50 mM Tris/HCl(pH 8.0), 5 mM EDTA, 5 mM EGTA) followed by 5 column volumes of wash buffer containing additionally 0.9% NaCl and finally re-equilibrated in salt-free wash buffer before eluting with 50 mM diethylamine in wash buffer at pH 11.5. The protein solution was neutralised with solid glycine and then further purified by loading the protein on a polyacrylamide gel and eluting the bands with a relative molecular weight of 65 to 80 kD and 40 to 42 kD, i.e. the bands representing the affinity purified 2.13 antigen (see above), after electrophoresis by electroelution using methods well known in the art. The purified protein was used for immunizing monkeys.

Monkey Protection Studies

Each of four *S. sciureus* monkeys was injected at day 0, day 24 and day 48 subcutaneously with one ml of emulsion containing a total of 65 µg purified 2.13 antigen (=vaccine). For the first injection the antigen was emulsified in Freund's complete adjuvant, whereas for the second and third injections the antigen was emulsified in Freund's incomplete adjuvant. A second group of four S. sciureus monkeys serving as control group was injected in a similar way with Freund's adjuvant mixed with phosphate buffered saline. 60 days after the first injection the animals were injected intravascularly with $3.5\times10^7$ parasitized red blood cells of a S. sciureus monkey which had been infected with the Palo Alto strain of *P. falciparum*. The subsequent parasitemia was evaluated by daily sampling of blood obtained by taking blood from the ear of the monkeys. Percentage of parasitemia was determined by scoring the number of parasitized red blood cells under the microscope in 200 optical fields each containing approximately 200 red blood cells. Animals exhibiting 20% parasitemia received drug therapy. It was found that 3 out of 4 monkeys did not require therapy and were therefore protected by the vaccine containing the 2.13 antigen.

Modifications and variations of this invention may be made without departing from the spirit and scope, as will be apparent to those skilled in the art. The specific embodiment herein is offered only as an example, and the invention is to be limited only by the claims.

What is claimed is:

1. An isolated DNA sequence encoding a *Plasmodium falciparum* antigen associated with the rhoptry organelles of the merozoite form of the malaria parasite, wherein said antigen has a molecular weight of about 80,000 Daltons and comprises the amino acid sequence M S F Y L G S L V I I F H V L F R N V A D G I N V N G D N N Y
G K T I I N N D F N F D D Y N Y W T P I N K K E F L N S Y E D
E F S S E S F L E N K S S V D D G N I N L T D T S T S N K S S
K K G H G R S R V R S A S A A A I L E E D D S K D D M E F K A
S P S V V K T S T P S G T Q T S G L K S S S P S S T K S S S P
S N V K S A S P H G E S N S S E E S T T K S S K R S A S V A G
I V G A D E E A P P A P K N T L T P L E E L Y P T N V N L F N
Y K Y S L N N M E E N I N I L K N E G D L V A Q K E E F E Y D
E N M E K A K Q D K K K A L E K I G K Q S D E E P F M F S E N
K F L E N Q V K E R N V A G S F S R F F S K L N P F K K D E V
I E K T E V S K K T F S G I G F N L T D K E A K V L G V G A T
Y Q E Y P E T M L Y N C P N N S N L F D T I E S L Q G R I I D I K K R E S M I S T T F E Q Q K E C L K N M G V L D L E L N D
T Q C K F G T C I G S F G E H H L R L Y E F E N D L F K F H P
N I D Y L T L A D G Y K L Q K N H I Y E L S H V N F C L L N P
K T L E E F L K K K E I K D L M G G D D L I K Y K E N F D N F
M S I S I T C H I E S L I Y D D I E A S Q D I A A V L K I A K
S K L H V I T S G L S Y K A R K L V Y K I Y S E I Q K N P D E
L Y E K L T W I Y D N I Y M I K R Y Y T A Y A L E G V C S Y L
E H D K S Q M Y T E L H I Y N K I V D S V R Y Y S S C F K N V
I V Y N A I I S G I H E K I K H F L K L V P R H N F L L D Y H
F N S I F E K E I K P A K K Y S T S H I Y F D P T V A S Y A Y
Y N L D R R T M V T I I N D Y F E A K K K E L T V I V S R M K
T D M L S L Q N E E S K I P N D K S A N S K L A T R L M K K F
K A E I R D F F K E M R I Q Y A K L I N I R Y R S H L K K N Y
F A F K R L D.

2. A DNA sequence according to claim 1 comprising the nucleotide sequence ATG AGT TTC TAT TTG GGT AGC TTA GTA ATA ATA TTC CAT GTA CTC TTC CGT AAT GTC GCT
GAT GGT ATA AAT GTA AAC GGA GAT AAT AAT TAT GGG AAA ACA ATA ATC AAT AAT GAT TTC
AAT TTT GAT GAT TAC AAT TAT TGG ACA CCA ATA AAT AAA AAG GAA TTT TTA AAT TCC TAT
GAA GAT GAA TTT TCA AGT GAA TCC TTT TTA GAA AAT AAA TCT AGT GTT GAT GAT GGA AAT
ATA AAT TTA ACA GAT ACA AGT ACA TCA AAT AAA AGT TCT AAA AAA GGA CAT GGT AGA AGT
AGA GTA AGA TCA GCA TCA GCT GCT GCA ATT CTT GAA GAA GAT GAT TCA AAA GAT GAT ATG -continued

GAATTTAAAGCTTCTCCTTCAGTTGTTAAAACATCTACTCCATCAGGTACACAGACATCT

GGTTTAAAATCATCTAGTCCATCTAGTACAAAGTCATCAAGTCCATCAAATGTAAAATCA

GCTAGTCCACATGGTGAATCTAATTCTTCTGAAGAAAGTACTACTAAATCCTCAAAGAGA

AGTGCTTCGGTTGCAGGTATTGTAGGTGCCGACGAAGAAGCACCTCCTGCACCAAAAAAC

ACCCTCACTCCATTAGAAGAATTATATCCTACTAATGTTAATTTATTTAACTATAAATAT

TCATTAAACAATATGGAAGAAAATATCAATATACTTAAAAACGAAGGAGATTTAGTTGCA

CAAAAAGAAGAATTTGAATATGATGAAAATATGGAAAAAGCTAAACAAGACAAAAAAAAA

GCACTTGAGAAAATAGGAAAACAATCAGACGAAGAACCTTTTATGTTTTCAGAAAATAAA

TTTCTTGAAAATCAAGTAAAAGAAAGAAATGTTGCTGGATCCTTTTCTCGATTTTTCAGT

AAATTAAATCCTTTTAAGAAAGATGAAGTAATAGAAAAAACTGAAGTATCAAACAAAACA

TTTTCAGGTATAGGTTTTAATCTTACTGACAAAGAAGCTAAAGTATTAGGTGTAGGTGCA

ACCTATCAAGAATATCCAGAAACCATGTTATATAACTGTCCAAACAATTCTAATTTGTTT

GATACTATAGAATCATTACAAGGAAGAATAATTGATATTAAAAAAAGAGAAAGCATGATA

TCAACAACTTTCGAACAACAAAAAGAATGTTTAAAAAATATGGGTGTACTTGATCTTGAA

TTAAACGATACACAATGTAAATTTGGTACATGTATAGGTAGCTTTGGAGAACATCATCTT

AGATTATACGAATTTGAGAATGACTTATTTAAATTTCATCCAAATATTGATTATTTAACT

TTAGCTGATGGATATAAATTACAAAAAAATCATATATATGAATTATCCCATGTAAACTTT

TGCTTATTAAATCCTAAAACATTAGAAGAATTTTTAAAAAAAAAAGAAATCAAGGATCTT

ATGGGTGGTGATGATCTTATAAAATATAAAGAAAATTTTGATAACTTTATGAGTATATCT

ATAACATGCCATATTGAATCTTTAATATATGATGATATTGAAGCATCTCAAGATATTGCT

GCTGTATTAAAAATTGCTAAAAGTAAATTACATGTAATAACATCAGGTTTATCATATAAA

GCAAGAAAATTAGTATATAAAATTTATAGTGAAATTCAAAAAAATCCAGATGAACTCTAT

GAAAAATTAACATGGATTTATGATAATATCTATATGATTAAAAGATATTATACTGCATAT

GCTTTAGAAGGTGTCTGTTCATATCTTGAACATGATAAAAGTCAAATGTATACAGAATTA

CATATTTATAACAAAATAGTCGACTCTGTTCGTTATTATAGTTCATGCTTTAAAAACGTT

ATTGTTTATAATGCTATCATTTCTGGTATACATGAAAAAATAAAACATTTCTTAAAATTA

GTACCAAGACACAACTTTCTTTTGGATTATCACTTTAATTCAATTTTTGAAAAAGAAATT

AAACCAGCCAAAAAATATAGTACTTCACATATTTATTTTGATCCAACTGTTGCATCATAT

GCTTATTATAATTTAGATAGAAGAACCATGGTTACTATTATTAATGATTATTTCGAAGCA

AAAAAAAAAGAATTAACCGTTATAGTATCTCGTATGAAAACAGATATGCTCAGTCTTCAA

AATGAAGAATCAAAAATACCAAATGACAAAAGTGCAAATTCAAAACTAGCTACAAGATTA

ATGAAAAAATTTAAAGCTGAAATCAGAGATTTCTTCAAAGAAATGCGTATACAATATGCT

AAATTAATAAACATACGTTACAGATCTCACTTAAAGAAAAACTACTTTGCCTTCAAGAGA

TTAGATTAA.

3. A unicellular host organism containing a recombinant vector comprising the DNA sequence of claim 2 and which host organism is capable of expressing the DNA sequence.

4. An isolated DNA sequence encoding a polypeptide, which polypeptide has at least one determinant immunologically cross-reactive with determinants on a *Plasmodium falciparum* antigen associated with the rhoptry organelles of the merozoite form of the malaria parasite, which antigen is about 80,000 Daltons and which polypeptide comprises the amino acid sequence

D E F S S E S F L E N K S S V D D G N I N L T D T S T S N K S

-continued

S K K G H G R S R V R S A S A A A I L E E D D S K D D M E F K

A S P S V V K T S T P S G T Q T S G L K S S S P S S T K S S S

P S N V K S A S P H G E S N S S E E S T T K S S K R S A S V A

G I V G A D E E A P P A P K N T L T P L E E L Y P T N V N L F

N Y K Y S L N N M E E N I N I L K N E G D L V A Q K E E F E Y

D E N M E K A K Q D K K K A L E K I G K Q S D E E P F M F S E

N K F L E N Q V K E R N V A G S F S R F F S K L N P F K K D E

V I E K T E V S K K T F S G I G F N L T D K E A K V L G V G A

T Y Q E Y P E T M L Y N C P N N S N L F D T I E S L Q G R I I

D I K K R E S M I S T T F E Q Q K E C L K N M G V L D L E L N

D T Q C K F G T C I G S F G E H H L R L Y E F E N D L F K F H

P N I D Y L T L A D G Y K L Q K N H I Y E L S H V N F C L L N

P K T L E E F L K K K E I K D L M G G D D L I K Y K E N F D N

F M S I S I T C H I E S L I Y D D I E A S Q D I A A V L K I A

K S K L H V I T S G L S Y K A R K L V Y K I Y S E I Q K N P D

E L Y E K L T W I Y D N I Y M I K R Y Y T A Y A L E G V C S Y

L E H D K S Q M Y T E L H I Y N K I V D S V R Y Y S S C F K N

V I V Y N A I I S G I H E K I K H F L K L V P R H N F L L D Y

H F.

5. A DNA sequence according to claim 4 comprising the nucleotide sequence

AAGATGAATTTTCAAGTGAATCCTTTTTAGAAAATAAATCTAGTGTTGATGATGGAAATA

TAAATTTAACAGATACAAGTACATCAAATAAAAGTTCTAAAAAAGGACATGGTAGAAGTA

GAGTAAGATCAGCATCAGCTGCTGCAATTCTTGAAGAAGATGATTCAAAAGATGATATGG

AATTTAAAGCTTCTCCTTCAGTTGTTAAAACATCTACTCCATCAGGTACACAGACATCTG

GTTTAAAATCATCTAGTCCATCTAGTACAAAGTCATCAAGTCCATCAAATGTAAAATCAG

CTAGTCCACATGGTGAATCTAATTCTTCTGAAGAAAGTACTACTAAATCCTCAAAGAGAA

GTGCTTCGGTTGCAGGTATTGTAGGTGCCGACGAAGAAGCACCTCCTGCACCAAAAAACA

CCCTCACTCCATTAGAAGAATTATATCCTACTAATGTTAATTTATTTAACTATAAATATT

CATTAAACAATATGGAAGAAAATATCAATATACTTAAAAACGAAGGAGATTTAGTTGCAC

AAAAAGAAGAATTTGAATATGATGAAAATATGGAAAAAGCTAAACAAGACAAAAAAAAAG

CACTTGAGAAAATAGGAAAACAATCAGACGAAGAACCTTTTATGTTTTCAGAAAATAAAT

-continued

TTCTTGAAAATCAAGTAAAAGAAAGAAATGTTGCTGGATCCTTTTCTCGATTTTTCAGTA
AATTAAATCCTTTTAAGAAAGATGAAGTAATAGAAAAAACTGAAGTATCAAAGAAAACAT
TTTCAGGTATAGGTTTTAATCTTACTGACAAAGAAGCTAAAGTATTAGGTGTAGGTGCAA
CCTATCAAGAATATCCAGAAACCATGTTATATAACTGTCCAAACAATTCTAATTTGTTTG
ATACTATAGAATCATTACAAGGAAGAATAATTGATATTAAAAAAAGAGAAAGCATGATAT
CAACAACTTTCGAACAACAAAAAGAATGTTTAAAAAATATGGGTGTACTTGATCTTGAAT
TAAACGATACACAATGTAAATTTGGTACATGTATAGGTAGCTTTGGAGAACATCATCTTA
GATTATACGAATTTGAGAATGACTTATTTAAATTTCATCCAAATATTGATTATTTAACTT
TAGCTGATGGATATAAATTACAAAAAAATCATATATATGAATTATCCCATGTAAACTTTT
GCTTATTAAATCCTAAAACATTAGAAGAATTTTTAAAAAAAAAAGAAATCAAGGATCTTA
TGGGTGGTGATGATCTTATAAAATATAAAGAAAATTTTGATAACTTTATGAGTATATCTA
TAACATGCCATATTGAATCTTTAATATATGATGATATTGAAGCATCTCAAGATATTGCTG
CTGTATTAAAAATTGCTAAAAGTAAATTACATGTAATAACATCAGGTTTATCATATAAAG
CAAGAAAATTAGTATATAAAATTTATAGTGAAATTCAAAAAAATCCAGATGAACTCTATG
AAAAATTAACATGGATTTATGATAATATCTATATGATTAAAAGATATTATACTGCATATG
CTTTAGAAGGTGTCTGTTCATATCTTGAACATGATAAAAGTCAAATGTATACAGAATTAC
ATATTTATAACAAAATAGTCGACTCTGTTCGTTATTATAGTTCATGCTTTAAAAACGTTA
TTGTTTATAATGCTATCATTTCTGGTATACATGAAAAAATAAAACATTTCTTAAAATTAG
TACCAAGACACAACTTTCTTTTGGATTATCACTTT.

6. A unicellular host organism containing a recombinant vector comprising the DNA sequence of claim 5 and which host organism is capable of expressing the DNA sequence.

* * * * *